(12) United States Patent
Hon

(10) Patent No.: US 12,150,478 B2
(45) Date of Patent: Nov. 26, 2024

(54) ELECTRONIC CIGARETTE

(71) Applicant: FONTEM VENTURES B.V., Amsterdam (NL)

(72) Inventor: Lik Hon, Beijing (CN)

(73) Assignee: FONTEM VENTURES B.V., Amsterdam (NL)

( * ) Notice: Subject to any disclaimer, the term of this patent is extended or adjusted under 35 U.S.C. 154(b) by 910 days.

(21) Appl. No.: 17/129,897

(22) Filed: Dec. 21, 2020

(65) Prior Publication Data

US 2021/0106053 A1   Apr. 15, 2021

Related U.S. Application Data

(60) Continuation of application No. 15/167,690, filed on May 27, 2016, now abandoned, which is a
(Continued)

(30) Foreign Application Priority Data

May 16, 2006   (CN) .......................... 200620090805.0

(51) Int. Cl.
*A24F 40/40* (2020.01)
*A24F 40/10* (2020.01)
(Continued)

(52) U.S. Cl.
CPC .............. *A24F 40/40* (2020.01); *A24F 40/46* (2020.01); *A24F 40/90* (2020.01); *F22B 1/284* (2013.01);
(Continued)

(58) Field of Classification Search
CPC ........ A24F 40/00; A24F 47/008; A24F 42/20; A61M 16/18
See application file for complete search history.

(56) References Cited

U.S. PATENT DOCUMENTS

| | | |
|---|---|---|
| 1,147,416 A | 7/1915 | MacDonald |
| 1,775,947 A | 9/1930 | Robinson |

(Continued)

FOREIGN PATENT DOCUMENTS

| | | |
|---|---|---|
| CN | 2047485 U | 11/1989 |
| CN | 2084236 U | 9/1991 |

(Continued)

OTHER PUBLICATIONS

Philip Morris Products S.A., Opposition of EP3061359, Opposer's Reply to Fontem's Grounds of Appeal, May 17, 2022.
(Continued)

*Primary Examiner* — Nathaniel E Wiehe
*Assistant Examiner* — Spencer H. Kirkwood
(74) *Attorney, Agent, or Firm* — Perkins Coie LLP; Kenneth H. Ohriner

(57) ABSTRACT

An electronic cigarette includes a battery assembly and an atomizer assembly within a housing with the battery assembly electrically connected to the atomizer assembly. The housing has one or more air inlets. A liquid storage component is in contact with a porous component of the atomizer assembly, with the porous component having a run-through hole. A heating wire is in an air flow path through the run-through hole.

5 Claims, 8 Drawing Sheets

Related U.S. Application Data continuation of application No. 13/740,011, filed on Jan. 11, 2013, now Pat. No. 9,456,632, which is a continuation of application No. 13/079,937, filed on Apr. 5, 2011, now Pat. No. 8,365,742, which is a division of application No. 12/226,818, filed as application No. PCT/CN2007/001575 on May 15, 2007, now Pat. No. 8,156,944.

(51) Int. Cl.
```
A24F 40/46      (2020.01)
A24F 40/90      (2020.01)
F22B 1/28       (2006.01)
H01M 10/0525    (2010.01)
H01M 10/42      (2006.01)
H01M 10/46      (2006.01)
H01M 10/48      (2006.01)
H01M 50/202     (2021.01)
H01M 50/213     (2021.01)
H01M 50/224     (2021.01)
H01M 50/247     (2021.01)
H01M 50/284     (2021.01)
H02J 7/00       (2006.01)
H05B 1/02       (2006.01)
H05B 3/03       (2006.01)
H05B 3/06       (2006.01)
H05B 3/42       (2006.01)
```

(52) U.S. Cl.
CPC ..... *H01M 10/0525* (2013.01); *H01M 10/425* (2013.01); *H01M 10/46* (2013.01); *H01M 10/488* (2013.01); *H01M 50/202* (2021.01); *H01M 50/213* (2021.01); *H01M 50/224* (2021.01); *H01M 50/247* (2021.01); *H01M 50/284* (2021.01); *H02J 7/00* (2013.01); *H02J 7/0042* (2013.01); *H05B 1/0244* (2013.01); *H05B 1/0291* (2013.01); *H05B 1/0297* (2013.01); *H05B 3/03* (2013.01); *H05B 3/06* (2013.01); *H05B 3/42* (2013.01); *A24F 40/10* (2020.01); *H01M 2220/30* (2013.01)

(56) References Cited

U.S. PATENT DOCUMENTS

| | | | |
|---|---|---|---|
| 1,968,509 | A | 7/1934 | Tiffany |
| 2,057,353 | A | 10/1936 | Whittemore |
| 2,104,266 | A | 1/1938 | McCormick |
| 2,597,195 | A | 5/1952 | Smith |
| 2,631,219 | A | 3/1953 | Suchy |
| 3,200,819 | A * | 8/1965 | Gilbert ............... A24F 40/485 131/273 |
| 3,431,393 | A | 3/1969 | Katsuda |
| 3,479,561 | A | 11/1969 | Janning |
| 3,551,643 | A | 12/1970 | Pricenski |
| 3,685,522 | A | 8/1972 | Kleinhans |
| 3,934,117 | A | 1/1976 | Schladitz |
| 4,171,000 | A | 10/1979 | Uhle |
| 4,207,457 | A | 6/1980 | Haglund |
| 4,228,925 | A | 10/1980 | Mendelovich |
| 4,284,089 | A | 8/1981 | Ray |
| 4,641,053 | A | 2/1987 | Takeda |
| 4,735,217 | A | 4/1988 | Gerth |
| 4,756,318 | A | 7/1988 | Clearman |
| 4,771,295 | A | 9/1988 | Baker |
| 4,771,796 | A | 9/1988 | Myer |
| 4,819,665 | A | 4/1989 | Roberts |
| 4,848,374 | A | 7/1989 | Chard |
| 4,907,606 | A | 3/1990 | Lilja |
| 4,922,901 | A * | 5/1990 | Brooks ............... A61M 16/109 131/273 |
| 4,945,929 | A | 8/1990 | Egilmex |
| 4,945,931 | A | 8/1990 | Gori |
| 4,947,874 | A | 8/1990 | Brooks |
| 4,947,875 | A | 8/1990 | Brooks |
| 4,968,263 | A | 11/1990 | Silbernagel |
| 4,981,522 | A | 1/1991 | Nichols |
| 5,042,470 | A | 8/1991 | Kanesaka |
| 5,060,671 | A | 10/1991 | Counts |
| 5,080,114 | A | 1/1992 | Rudolph |
| 5,095,921 | A | 3/1992 | Losee |
| 5,117,482 | A | 5/1992 | Hauber |
| 5,144,962 | A | 11/1992 | Counts |
| 5,159,940 | A | 11/1992 | Hayward |
| 5,190,060 | A | 7/1993 | Gerding |
| 5,224,498 | A | 10/1993 | Deevi |
| 5,249,586 | A | 11/1993 | Morgan |
| 5,261,424 | A | 11/1993 | Sprinkel, Jr. |
| 5,266,746 | A | 11/1993 | Nishihara |
| 5,285,798 | A | 6/1994 | Banerjee |
| 5,322,075 | A | 6/1994 | Deevi |
| 5,388,594 | A | 8/1995 | Counts |
| 5,438,978 | A | 8/1995 | Hardester, III |
| 5,497,791 | A | 4/1996 | Bowen |
| 5,505,214 | A | 4/1996 | Collins |
| 5,512,001 | A | 4/1996 | Kent |
| 5,591,368 | A | 1/1997 | Fleischhauer |
| 5,666,977 | A | 9/1997 | Higgins |
| 5,666,978 | A | 9/1997 | Counts |
| 5,703,633 | A | 12/1997 | Gehrer |
| 5,730,158 | A | 3/1998 | Collins |
| 5,743,251 | A * | 4/1998 | Howell ............... A61M 11/001 239/10 |
| 5,746,251 | A | 5/1998 | Bullard |
| 5,799,663 | A | 9/1998 | Gross |
| 5,819,756 | A | 10/1998 | Mielordt |
| 5,865,185 | A | 2/1999 | Collins |
| 5,878,752 | A | 3/1999 | Adams |
| 5,894,841 | A | 4/1999 | Voges |
| 5,944,025 | A | 8/1999 | Cook |
| 6,010,334 | A | 1/2000 | Mifune |
| 6,040,560 | A | 3/2000 | Fleischhauer |
| 6,041,789 | A | 3/2000 | Bankert |
| 6,095,153 | A | 8/2000 | Kessler |
| 6,125,853 | A | 10/2000 | Susa |
| 6,155,268 | A | 12/2000 | Takeuchi |
| 6,164,287 | A | 12/2000 | White |
| 6,178,969 | B1 | 1/2001 | St. Charles |
| 6,196,218 | B1 | 3/2001 | Voges |
| 6,234,167 | B1 | 5/2001 | Cox |
| 6,354,293 | B1 | 3/2002 | Madison |
| 6,357,671 | B1 | 3/2002 | Cewers |
| 6,443,146 | B1 | 9/2002 | Voges |
| 6,532,965 | B1 | 3/2003 | Abhulimen |
| 6,557,552 | B1 | 5/2003 | Cox |
| 6,598,607 | B2 | 7/2003 | Adiga |
| 6,601,776 | B1 | 8/2003 | Oljaca |
| 6,681,998 | B2 | 1/2004 | Sharpe |
| 6,715,494 | B1 | 4/2004 | McCoy |
| 6,772,756 | B2 | 8/2004 | Shayan |
| 6,803,545 | B2 | 10/2004 | Blake |
| 6,810,883 | B2 | 11/2004 | Felter |
| 6,854,461 | B2 | 2/2005 | Nichols |
| 6,854,470 | B1 | 2/2005 | Pu |
| 7,100,618 | B2 | 9/2006 | Dominguez |
| 7,131,599 | B2 | 11/2006 | Katase |
| 7,726,320 | B2 | 6/2010 | Robinson |
| 7,832,410 | B2 | 11/2010 | Hon |
| 7,845,359 | B2 | 12/2010 | Montaser |
| 7,997,280 | B2 | 8/2011 | Rosenthal |
| 8,156,944 | B2 | 4/2012 | Han |
| 10,010,109 | B2 | 7/2018 | Janardhan et al. |
| 2003/0033055 | A1 | 2/2003 | McCrae |
| 2003/0108342 | A1 | 6/2003 | Sherwood |
| 2003/0150451 | A1 | 8/2003 | Shayan |
| 2004/0089314 | A1 | 5/2004 | Felter |
| 2004/0149282 | A1 | 8/2004 | Hickle |
| 2004/0182403 | A1 | 9/2004 | Andersson |
| 2004/0261802 | A1 | 12/2004 | Griffin |
| 2005/0016550 | A1 | 1/2005 | Katase |

(56) References Cited

U.S. PATENT DOCUMENTS

| | | |
|---|---|---|
| 2005/0236006 A1 | 10/2005 | Cowan |
| 2006/0032242 A1 | 2/2006 | TeGrotenhuis |
| 2006/0175425 A1 | 8/2006 | McGee |
| 2006/0191546 A1 | 8/2006 | Takano |
| 2006/0196518 A1 | 9/2006 | Hon |
| 2007/0107879 A1* | 5/2007 | Radomski ............ A61M 16/18 165/104.26 |
| 2007/0267031 A1 | 11/2007 | Hon |
| 2008/0276947 A1 | 11/2008 | Martzel |
| 2009/0095311 A1 | 4/2009 | Hon |
| 2009/0126745 A1 | 5/2009 | Hon |
| 2009/0151717 A1 | 6/2009 | Bowen |
| 2009/0188490 A1 | 7/2009 | Han |
| 2009/0230117 A1 | 9/2009 | Fernand |
| 2009/0260642 A1 | 10/2009 | Monsees |
| 2009/0272379 A1 | 11/2009 | Thorens |
| 2010/0031968 A1 | 2/2010 | Sheikh |
| 2010/0126505 A1 | 5/2010 | Rinker |
| 2010/0181387 A1 | 7/2010 | Zaffaroni |
| 2010/0200008 A1 | 8/2010 | Taieb |
| 2010/0242974 A1 | 9/2010 | Pan |
| 2010/0307518 A1 | 12/2010 | Wang |
| 2011/0005535 A1 | 1/2011 | Xiu |
| 2011/0011396 A1 | 1/2011 | Fang |
| 2011/0036346 A1 | 2/2011 | Cohen |
| 2012/0111347 A1 | 5/2012 | Hon |
| 2020/0205474 A1 | 7/2020 | Tong |

FOREIGN PATENT DOCUMENTS

| | | | | |
|---|---|---|---|---|
| CN | 1135860 | A | | 11/1996 |
| CN | 1196660 | A | | 11/1996 |
| CN | 2293957 | Y | | 10/1998 |
| CN | 1233436 | A | | 11/1999 |
| CN | 1252961 | A | | 5/2000 |
| CN | 1575673 | A | * | 2/2005 ........... A24F 47/002 |
| CN | 2719043 | Y | | 8/2005 |
| CN | 2777995 | Y | | 5/2006 |
| CN | 2870485 | Y | | 2/2007 |
| CN | 2887086 | U | | 4/2007 |
| CN | 101116542 | A | | 2/2008 |
| CN | 101176805 | A | | 5/2008 |
| CN | 201067079 | Y | | 6/2008 |
| CN | 201079011 | Y | | 7/2008 |
| CN | 201085044 | Y | | 7/2008 |
| CN | 201379072 | Y | | 1/2010 |
| CN | 201797997 | U | | 4/2011 |
| CN | 202026802 | U | | 11/2011 |
| CN | 202026804 | U | | 11/2011 |
| DE | 10051792 | A1 | | 5/2002 |
| DE | 102006004484 | | | 8/2007 |
| EP | 0057243 | A1 | | 8/1982 |
| EP | 0192950 | A1 | | 3/1986 |
| EP | 0230420 | A1 | | 8/1987 |
| EP | 0125210 | B1 | | 12/1987 |
| EP | 0295122 | A2 | | 12/1988 |
| EP | 0358002 | A2 | | 3/1990 |
| EP | 0545186 | A2 | | 6/1993 |
| EP | 0824927 | A2 | | 2/1998 |
| EP | 0845220 | A1 | | 6/1998 |
| EP | 0893071 | A1 | | 1/1999 |
| EP | 0951219 | A1 | | 10/1999 |
| EP | 0703735 | B1 | | 7/2001 |
| EP | 2018886 | A1 | | 1/2009 |
| GB | 588117 | | | 5/1947 |
| JP | H0593516 | A | | 4/1993 |
| WO | 1998017130 | A1 | | 4/1998 |
| WO | 2002061701 | A1 | | 8/2002 |
| WO | 2003034847 | A1 | | 5/2003 |
| WO | WO-03070031 | A1 | * | 8/2003 ............ A24D 1/02 |
| WO | 2004080216 | | | 9/2004 |
| WO | 2005099494 | A1 | | 10/2005 |
| WO | 2006124757 | | | 11/2006 |
| WO | 2007078273 | | | 7/2007 |

OTHER PUBLICATIONS

USPTO, Non-Final Office Action for U.S. Appl. No. 15/167,690 dated Jun. 17, 2021, 49 pages.
EPO, Opposition of EP2789250 (Application No. 14155503.7) Decision Revoking European Patent No. 2789250, Apr. 27, 2021.
EPO, Opposition of EP3061359 (Application No. 16158159.0) Decision Revoking European Patent No. 3061359, May 4, 2021.
Philip Morris Products S.A., Opposition of EP2789250, Written Submission, Feb. 26, 2021.
Philip Morris Products S.A., Opposition of EP2789250, Written Submission, Apr. 26, 2021.
Philip Morris Products S.A., Opposition of EP3061359, Written Submission, Mar. 3, 2021.
Philip Morris Products S.A., Opposition of EP3061359, Written Submission, Apr. 30, 2021.
U.S. Appl. No. 15/996,969, Interview Summary, Feb. 16, 2021.
U.S. Appl. No. 15/996,969, Notice of Allowance, May 10, 2021.
USPTO, Final Office Action dated Jan. 7, 2022 for U.S. Appl. No. 15/167,690, 30 pages.
Adares Patent—Und Rechtsanwalte Reininger & Partner GmbH, Opposition to European Patent No. EP2789250, Sep. 26, 2019.
CB Distributors Inc. and DR Distributors, LLC, Petition for Inter Partes Review of U.S. Pat. No. 8,156,944—IPR2013-00387, Jun. 27, 2013.
CB Distributors Inc. and DR Distributors, LLC, IPR2013-00387, Ex. 1001—U.S. Pat. No. 8,156,944 to Han, Jun. 27, 2013.
CB Distributors Inc. and DR Distributors, LLC, IPR2013-00387, Ex. 1002—Request for Certificate of Correction dated Jun. 11, 2012, Jun. 27, 2013.
CB Distributors Inc. and DR Distributors, LLC, IPR2013-00387, Ex. 1003—WO 2007/131449 A1 to Hon, Jun. 27, 2013.
CB Distributors Inc. and DR Distributors, LLC, IPR2013-00387, Ex. 1004—CN Patent No. 2719043, Jun. 27, 2013.
CB Distributors Inc. and DR Distributors, LLC, IPR2013-00387, Ex. 1005—CN Patent Application No. 200620090805, Jun. 27, 2013.
CB Distributors Inc. and DR Distributors, LLC, IPR2013-00387, Ex. 1006—Certified English Translation of CN Patent Application No. 200620090805 dated Oct. 6, 2011, Jun. 27, 2013.
CB Distributors Inc. and DR Distributors, LLC, IPR2013-00387, Ex. 1007—WO 2004/095955 A1 to Hon, Jun. 27, 2013.
CB Distributors Inc. and DR Distributors, LLC, IPR2013-00387, Ex. 1008—WO 2005/099494 A1 to Hon, Jun. 27, 2013.
CB Distributors Inc. and DR Distributors, LLC, IPR2013-00387, Ex. 1009—Certified English Translation of WO 2005/099494 A1 to Hon dated Jun. 17, 2013, Jun. 27, 2013.
CB Distributors Inc. and DR Distributors, LLC, IPR2013-00387, Ex. 1010—Office Action dated Feb. 2, 2011, Jun. 27, 2013.
CB Distributors Inc. and DR Distributors, LLC, IPR2013-00387, Ex. 1011—Response to Office Action dated Feb. 22, 2011, Jun. 27, 2013.
CB Distributors Inc. and DR Distributors, LLC, IPR2013-00387, Ex. 1012—Office Action dated Apr. 12, 2011, Jun. 27, 2013.
CB Distributors Inc. and DR Distributors, LLC, IPR2013-00387, Ex. 1013—Response to Office Action dated Oct. 12, 2011, Jun. 27, 2013.
CB Distributors Inc. and DR Distributors, LLC, IPR2013-00387, Ex. 1014—Inter Partes Reexamination Request dated Sep. 13, 2012, Jun. 27, 2013.
CB Distributors Inc. and DR Distributors, LLC, IPR2013-00387, Ex. 1015—Order Granting Reexamination dated Nov. 27, 2012, Jun. 27, 2013.
CB Distributors Inc. and DR Distributors, LLC, IPR2013-00387, Ex. 1016—Office Action dated Nov. 27, 2012, Jun. 27, 2013.
CB Distributors Inc. and DR Distributors, LLC, IPR2013-00387, Ex. 1017—Response to Office Action dated Jan. 28, 2013, Jun. 27, 2013.
CB Distributors Inc. and DR Distributors, LLC, IPR2013-00387, Ex. 1018—Third Party Response dated Feb. 27, 2013, Jun. 27, 2013.
CB Distributors Inc. and DR Distributors, LLC, IPR2013-00387, Ex. 1019—WO 2007/078273 A1 to Liu, Jun. 27, 2013.

(56) References Cited

OTHER PUBLICATIONS

CB Distributors Inc. and DR Distributors, LLC, IPR2013-00387, Ex. 1020—EP 0845220 A1 to Susa et al., Jun. 27, 2013.
Collins, John M., *Fontem* v. *NJOY, Inc.*, Case 14-cv-01645 GW (MRW) and consolidated cases, Expert Report—Invalidity (Excerpts), Jun. 18, 2015.
Collins, John M., *Fontem* v. *NJOY, Inc.*, Case 14-cv-01645 GW (MRW) and consolidated cases, Expert Report—Invalidity, Appendix E-'742, Jun. 18, 2015.
Eisenfuhr Speiser Part GMBH, Opposition to European Patent No. EP2022349, Apr. 30, 2015.
Eisenfuhr Spieser Part GMBH, Opposition to EP2022349—Additional Observations, Aug. 5, 2016.
Eisenfuhr Spieser Part GMBH, Opposition to EP2022349—Additional Observations, Annex 1—Affidavit of Aimei Xu, Aug. 5, 2016.
EPO, Application No. EP07721148, Extended European Search Report, Dec. 6, 2010.
EPO, Application No. EP11001479, Extended European Search Report, Jul. 4, 2011.
EPO, Application No. EP14155503.7, Examination Report, Oct. 25, 2017, 5 pgs.
EPO, Application No. EP14155503.7, Extended European Search Report, Feb. 3, 2015.
EPO, Application No. EP14155503.7, Partial European search report, Sep. 1, 2014.
EPO, Application No. EP14173781.7, Extended European Search Report, Apr. 22, 2015.
EPO, Application No. EP16158159.0, Extended European Search Report, Jul. 12, 2016.
EPO, Opposition of EP2022349, Summons to Attend Oral Proceedings, Aug. 13, 2018.
EPO, Decision Revoking European Patent No. EP2022349, Oct. 17, 2016.
EPO, Appeal of Opposition of EP2022349, Board Communication, Dec. 13, 2019.
EPO, Opposition of EP2878215 (Application No. 14173781.7), Exam Report, Nov. 23, 2017.
EPO, Opposition of EP2878215 (Application No. 14173781.7), Provisional Decision in advance of Oral Hearing, Aug. 13, 2018.
EPO, Decision Revoking European Patent No. 2878215, Jul. 10, 2019.
EPO, Opposition of EP2789250 (Application No. 14155503.7) Provisional Opinion and Summons to Attend Oral Proceedings, Jul. 23, 2020.
EPO, Opposition of EP3061359 (Application No. 16158159.0) Provisional Opinion and Summons to Attend Oral Proceedings, Jul. 27, 2020.
Fin Branding Group, LLC, Request for Inter Partes Reexamination of U.S. Pat. No. 8,156,944, Sep. 13, 2012.
Fin Branding Group, LLC, Third Party Submission in U.S. Appl. No. 95/002,235 incl Oljaca 6601776, Feb. 27, 2013.
Fontem Holdings 1 B.V., Opposition of EP2878215, Patent Owner Request for Revocation of Patent, May 10, 2019.
High Court of Justice, Britain, Approved Judgment Revoking EP(UK)2022349, Sep. 2, 2016.
Insmoke AG, Opposition to European Patent No. EP2022349, Apr. 28, 2015.
Intellectual Property Office of New Zealand, Application No. NZ572309, Exam Report, Apr. 21, 2010.
IP Office Australia, Application No. AU2007250367, Patent Examination Report No. 1, Jul. 30, 2012.
IP Office Australia, Application No. AU2014208287, Patent Examination Report No. 1, Aug. 5, 2016, 4 pgs.
IP Office China, China PRC, Application No. PCT/CN07/001575, English Translation of Written Opinion, Jul. 20, 2007.
IP Office China, China PRC, Application No. PCT/CN07/001575, International Search Report, Aug. 16, 2007.
IP Office China, China PRC, Utility Model Patent ZL 200620090805.0, Search Report, Nov. 18, 2008.
IP Office China, China PRC, Decision of Patent Invalidation Petition, CN200720148285.9, with English Translation, Oct. 31, 2014.
IP Office India, Application No. IN8528/DELNP/2008, First Examination Report, Mar. 27, 2014.
IP Office India, Application No. IN3528/DELNP/2008, Decision of Refusal, Jul. 18, 2017.
IP Office Israel, Application No. IL194768, Office Action, Nov. 12, 2014.
IP Office Korea, Application No. KR10-2008-7026879, Office Action, Jun. 9, 2011.
IP Office Mexico, Application No. MX/a/2008/013526, Exam Report, Jul. 15, 2011.
IP Office Mexico, Application No. MX/a/2017/009524, Office Action, May 3, 2018.
ITC Limited, Opposition to Grant of Indian Patent Application No. 8528/DELNP/2008, served on Applicant's Indian Counsel Oct. 18, 2016 (filed Sep. 10, 2014).
ITC Limited, Opposition to Grant of Indian Patent Application No. 8528/DELNP/2008, Annexure A—Complete specification as filed of impugned application No. 8528/DELNP/2008, Sep. 10, 2014.
ITC Limited, Opposition to Grant of Indian Patent Application No. 8528/DELNP/2008, Annexure A1—INPADOC family list for WO2007131449, Sep. 10, 2014.
ITC Limited, Opposition to Grant of Indian Patent Application No. 8528/DELNP/2008, Annexure A2—International Search Report and Preliminary Examination Report for PCT/CN2007/001575 (WO counterpart of impugned application), Sep. 10, 2014.
ITC Limited, Opposition to Grant of Indian Patent Application No. 8528/DELNP/2008, Exhibit 1—EP1736065 (English equivalent of CN2719043), Sep. 10, 2014.
ITC Limited, Opposition to Grant of Indian Patent Application No. 8528/DELNP/2008, Exhibit 2—U.S. Pat. No. 5,799,663, Sep. 10, 2014.
ITC Limited, Opposition to Grant of Indian Patent Application No. 8528/DELNP/2008, Exhibit 3—EP0845220, Sep. 10, 2014.
ITC Limited, Opposition to Grant of Indian Patent Application No. 8528/DELNP/2008, Exhibit 4—EP0951219, Sep. 10, 2014.
Joyetech Deutschland GMBH, Opposition to EP2022349, Mar. 10, 2015.
Joyetech Deutschland GMBH, Opposition to EP2022349—Additional Observations, Aug. 8, 2016.
Joyetech Deutschland GMBH, Opposition to EP2878215, Jan. 27, 2017.
Joyetech Deutschland GMBH, Opposition to EP2878215, D1—U.S. Pat. No. 2,057,353A, Jan. 27, 2017.
Joyetech Deutschland GMBH, Opposition to EP2878215, D2—EP0845220A, Jan. 27, 2017.
Joyetech Deutschland GMBH, Opposition to EP2878215, D3—CN2719043YA1, Jan. 27, 2017.
Joyetech Deutschland GMBH, Opposition to EP2878215, D3a—EP1736065A1, Jan. 27, 2017.
Joyetech Deutschland GMBH, Opposition to EP2878215, D3b—CN2719043Y—English Translation, Jan. 27, 2017.
Joyetech Deutschland GMBH, Opposition to EP2878215, D4—U.S. Pat. No. 3,934,117A, Jan. 27, 2017.
Joyetech Deutschland GMBH, Opposition to EP2878215, D5—U.S. Pat. No. 5,117,482A, Jan. 27, 2017.
Joyetech Deutschland GMBH, Opposition to EP2878215, D6—U.S. Pat. No. 6,681,998B2, Jan. 27, 2017.
Joyetech Deutschland GMBH, Opposition to EP2878215, D7—U.S. Pat. No. 6,557,552B1, Jan. 27, 2017.
Joyetech Deutschland GMBH, Opposition to EP2878215, D8—EP0703735B1, Jan. 27, 2017.
Joyetech Deutschland GMBH, Opposition to EP2878215, D9—EP0893071A1, Jan. 27, 2017.
Joyetech Deutschland GMBH, Opposition to EP2878215, D10—Wikepedia "Heating Element", Jan. 27, 2017.
Joyetech Deutschland GMBH, Opposition to EP2878215, D11—EP1618803A1, Jan. 27, 2017.
Joyetech Deutschland GMBH, Opposition to EP2878215, D12—EP0358114A2, Jan. 27, 2017.
Joyetech Deutschland GMBH, Opposition to EP2878215, D13—EP2018886A1, Jan. 27, 2017.

(56) References Cited

OTHER PUBLICATIONS

Joyetech Deutschland GMBH, Opposition to EP2878215, EP1—EP2878215B1, Jan. 27, 2017.
Joyetech Deutschland GMBH, Opposition to EP2878215, EP2—WO20070131449A1, Jan. 27, 2017.
Joyetech Deutschland GMBH, Opposition to EP2878215, EP2a—EP2022349A1 (Parent application), Jan. 27, 2017.
Joyetech Deutschland GMBH, Opposition to EP2878215, EP2b—WO20070131449A1 English Translation, Jan. 27, 2017.
Joyetech Deutschland GMBH, Opposition to EP2878215, EP2c—EP2878215A1 (published Engl. Language div appl.), Jan. 27, 2017.
Joyetech Deutschland GMBH, Opposition to EP2878215, EP2d Comparison of the Specifications of EP2878215A1 and EP2022349A1, Jan. 27, 2017.
Joyetech Deutschland GMBH, Opposition to EP2878215, EP3—of the priority application CN2006290805, Jan. 27, 2017.
Joyetech Deutschland GMBH, Opposition to EP2878215, EP3a—CN2006-20090805 (English Translation), Jan. 27, 2017.
Joyetech Deutschland GMBH, Opposition to EP2878215, EP4—Decision Revoking EP 2022349B1, Jan. 27, 2017.
Joyetech Deutschland GMBH, Opposition of EP2878215, Additional Observations, Mar. 22, 2019.
Joyetech Deutschland GmbH, Opposition to European Patent No. EP3061359, Jul. 3, 2019.
Joyetech Deutschland GmbH, Opposition to European Patent No. EP2789250, Sep. 26, 2019.
JT International S.A., Petition for Inter Partes Review of U.S. Pat. No. 8,365,742—IPR2015-01587, Paper 1, Jul. 14, 2015.
JT International S.A., IPR2015-01587, Ex. 1001, U.S. Pat. No. 8,365,742 ("'742 patent"), Jul. 14, 2015.
JT International S.A., IPR2015-01587, Ex. 1002, Declaration of Jeffrey A. Schuster, Ph.D., Jul. 14, 2015.
JT International S.A., IPR2015-01587, Ex. 1003, U.S. Pat. No. 6,155,268 ("Takeuchi"), Jul. 14, 2015.
JT International S.A., IPR2015-01587, Ex. 1004, U.S. Pat. No. 6,234,167 ("Cox"), 7/2142015.
JT International S.A., IPR2015-01587, Ex. 1005, U.S. Pat. No. 4,947,874 ("Brooks"), Jul. 14, 2015.
JT International S.A., IPR2015-01587, Ex. 1006, U.S. Pat. No. 2,057,353 ("Whittemore"), Jul. 14, 2015.
JT International S.A., IPR2015-01587, Ex. 1007, EP 0 845 220 ("Susa"), Jul. 14, 2015.
JT International S.A., IPR2015-01587, Ex. 1008, WO 2007/078273 A1 ("Liu"), Jul. 14, 2015.
JT International S.A., IPR2015-01587, Ex. 1009, '742 Prosecution History, Preliminary Amendment, Jul. 14, 2015.
JT International S.A., IPR2015-01587, Ex. 1010, '742 Prosecution History, Non-final Office Action, Jul. 14, 2015.
JT International S.A., IPR2015-01587, Ex. 1011, '742 Prosecution History, Amendment, Jul. 14, 2015.
JT International S.A., IPR2015-01587, Ex. 1012, '742 Prosecution History, Supplemental Amendment, Jul. 14, 2015.
JT International S.A., IPR2015-01587, Ex. 1013, '742 Prosecution History, Examiner Interview Summary, Jul. 14, 2015.
JT International S.A., IPR2015-01587, Ex. 1014, '742 Prosecution History, Notice of Allowance, Jul. 14, 2015.
JT International S.A., IPR2015-01587, Ex. 1015, '742 Prosecution History, Certificate of Correction, Jul. 14, 2015.
JT International S.A., IPR2015-01587, Ex. 1016, Fontem Litigation Joint Claim Construction Chart, Jul. 14, 2015.
JT International S.A., IPR2015-01587, Ex. 1017, Claim Construction Rulings in CV 14-1645, Jul. 14, 2015.
JT International S.A., IPR2015-01587, Ex. 1018, Webster's New World Collegiate Dictionary ("detach"), Jul. 14, 2015.
JT International S.A., IPR2015-01587, Ex. 1019, Oxford American Dictionary & Thesaurus ("frame"), Jul. 14, 2015.
JT International S.A., IPR2015-01587, Ex. 1020, McGraw-Hill Dictionary of Scientific and Technical Terms (5th ed. 1994) ("assembly") ("component") ("porous") , Jul. 14, 2015.
JT International S.A., IPR2015-01587, Ex. 1021, Academic Press Dictionary ("permeability") ("solid"), Jul. 14, 2015.
JT International S.A., IPR2015-01587, Ex. 1022, American Heritage Dictionary ("atomize") ("end") ("substantial"), Jul. 14, 2015.
JT International S.A., IPR2015-01587, Ex. 1023, Merriam-Webster.com ("aerosol") ("atomizer") ("permeable") ("porous"), Jul. 14, 2015.
JT International SA, Opposition to European Patent No. EP2022349, Apr. 30, 2015.
Khan, Sirajuddin, son of Kahn, Samsuddin, Opposition to Grant of Indian Patent Application No. 8528/DELNP/2008, Jun. 20, 2014.
Lang & Tomerius, Opposition to European Patent No. EP3061359, Jul. 3, 2019.
Nicoventures Holdings Limited, Opposition to European Patent No. EP2022349, Apr. 30, 2015.
Nicoventures Holdings Ltd., Application No. EP14173781.7, Third Party Observations, Jan. 13, 2016.
NJOY, Inc. et al., Defendants' Joint Invalidity Contentions, CV14-01645 etc., Aug. 7, 2014.
NJOY, Inc. et al., Defendants' Joint Invalidity Contentions, CV-14-01645 etc., Attachment A—Claim Charts for U.S. Pat. No. 8,365,742, Aug. 7, 2014.
NJOY, Inc., Declaration of Brent K. Yamashita in Support of Defendants' Motion for Leave to Amend Invalidity Contentions dated Jun. 29, 2015 and filed in *Fontem Ventures B.V.* v. *NJOY, Inc.*, U.S. District Court, Central District of California, Consolidated Case No. CV 14-01645 GW (MRW) and related consolidated cases.
NJOY, Inc., Exhibit 1 to Defendants' Motion for Leave to Amend Invalidity Contentions dated Jun. 29, 2015 and filed in *Fontem Ventures B.V.* v. *NJOY, Inc.*, U.S. District Court, Central District of California, Consolidated Case No. CV 14-01645 GW (MRW) and related consolidated cases.
NJOY, Inc., Exhibit 2 to Defendants' Motion for Leave to Amend Invalidity Contentions dated Jun. 29, 2015 and filed in *Fontem Ventures B.V.* v. *NJOY, Inc.*, U.S. District Court, Central District of California, Consolidated Case No. CV 14-01645 GW (MRW) and related consolidated cases.
NJOY, Inc., Exhibit 3 to Defendants' Motion for Leave to Amend Invalidity Contentions dated Jun. 29, 2015 and filed in *Fontem Ventures B.V.* v. *NJOY, Inc.*, U.S. District Court, Central District of California, Consolidated Case No. CV 14-01645 GW (MRW) and related consolidated cases.
NJOY, Inc. Exhibit 4 to Defendants' Motion for Leave to Amend Invalidity Contentions dated Jun. 29, 2015 and filed in *Fontem Ventures B.V.* v. *NJOY, Inc.*, U.S. District Court, Central District of California, Consolidated Case No. CV 14-01645 GW (MRW) and related consolidated cases.
NJOY, Inc. Exhibit 5 to Defendants' Motion for Leave to Amend Invalidity Contentions dated Jun. 29, 2015 and filed in *Fontem Ventures B.V.* v. *NJOY, Inc.*, U.S. District Court, Central District of California, Consolidated Case No. CV 14-01645 GW (MRW) and related consolidated cases.
NJOY, Inc., Memorandum of Points and Authorities in Support of Defendants' Motion for Leave to Amend Invalidity Contentions dated Jun. 29, 2015 and filed in *Fontem Ventures B.V.* v. *NJOY, Inc.*, U.S. District Court, Central District of California, Consolidated Case No. CV 14-01645 GW (MRW) and related consolidated cases.
NJOY, Inc., production documents VLACHOS 0000061-72; *Fontem Ventures B.V.* v. *NJOY, Inc.*, U.S. District Court, Central District of California, Consolidated Case No. CV 14-01645 GW (MRW) and related consolidated cases, Jun. 4, 2015.
NJOY, Inc., Reply Brief in Support of Defendants' Motion for Leave to Amend Invalidity Contentions dated Jul. 13, 2015 and filed in *Fontem Ventures B.V.* v. *NJOY, Inc.*, U.S. District Court, Central District of California, Consolidated Case No. CV 14-01645 GW (MRW) and related consolidated cases.
Nu Mark LLC, Answer to Complaint and Counterclaims in *Fontem Ventures B.V.* v. *Nu Mark LLC*, 16-CV-1259, Dkt. 034, Oct. 26, 2016.
Nu Mark LLC, Answer to Complaint and Counterclaims in *Fontem Ventures B.V.* v. *Nu Mark LLC*, 16-CV-2291, Dkt. 025, Jun. 27, 2016.

(56) References Cited

OTHER PUBLICATIONS

Nu Mark LLC, First Amended Answer and Counterclaims in *Fontem Ventures B.V. v. Nu Mark LLC*, 16-CV-2291, Dkt. 042, Jul. 28, 2016.
Nu Mark LLC, Petition for Inter Partes Review of U.S. Pat. No. 8,365,742—IPR2016-01303, Jun. 28, 2016.
Nu Mark LLC, IPR2016-01303, Ex.1001 U.S. Pat. No. 8,365,742 ("the 742 Patent"), Jun. 28, 2016.
Nu Mark LLC, IPR2016-01303, Ex.1002 Excerpts of the prosecution history for U.S. Pat. No. 8,365,742, Jun. 28, 2016.
Nu Mark LLC, IPR2016-01303, Ex.1003 Declaration of John M. Collins, Ph.D. ("Collins Decl."), Jun. 28, 2016.
Nu Mark LLC, IPR2016-01303, Ex.1004 U.S. Pat. No. 6,155,268 ("Takeuchi"), Jun. 28, 2016.
Nu Mark LLC, IPR2016-01303, Ex.1005 U.S. Pat. No. 2,057,353 ("Whittemore"), Jun. 28, 2016.
Nu Mark LLC, IPR2016-01303, Ex.1006 U.S. Pat. No. 4,947,874 ("Brooks"), Jun. 28, 2016.
Nu Mark LLC, IPR2016-01303, Ex.1007 Docket entry #65 from *Fontem Ventures, B.V.*, et al. v. *NJOY, Inc.*, et al., 2:14-cv-01645 (C.D. Cal.) ("Rulings on Claim Construction"), Jun. 28, 2016.
Nu Mark LLC, IPR2016-01303, Ex.1008 U.S. Patent Application No. 2006/0093977 A1 ("Pellizzari I"), Jun. 28, 2016.
Nu Mark LLC, IPR2016-01303, Ex.1009 U.S. Pat. No. 7,059,307 ("Pellizzari II"), Jun. 28, 2016.
Nu Mark LLC, IPR2016-01303, Ex.1010 U.S. Pat. No. 5,894,841 ("Voges"), Jun. 28, 2016.
Nu Mark LLC, IPR2016-01303, Ex.1011 U.S. Pat. No. 5,743,251 ("Howell"), Jun. 28, 2016.
Nu Mark LLC, IPR2016-01303, Ex.1012 U.S. Pat. No. 2,461,664 ("Smith"), Jun. 28, 2016.
Nu Mark LLC, IPR2016-01303, Ex.1013 U.S. Pat. No. 3,234,357 ("Eberhard"), Jun. 28, 2016.
Nu Mark LLC, IPR2016-01303, Ex.1014 U.S. Pat. No. 5,745,985 ("Ghosh"), Jun. 28, 2016.
Nu Mark LLC, IPR2016-01303, Ex.1015 U.S. Pat. No. 4,676,237 ("Wood"), Jun. 28, 2016.
Nu Mark LLC, IPR2016-01303, Ex.1016 U.S. Pat. No. 4,945,448 ("Bremenour"), Jun. 28, 2016.
Nu Mark LLC, IPR2016-01303, Ex.1017 U.S. Pat. No. 2,442,004 ("Hayward-Butt"), Jun. 28, 2016.
Nu Mark LLC, IPR2016-01303, Ex.1018 U.S. Pat. No. 3,200,819 ("Gilbert"), Jun. 28, 2016.
Nu Mark LLC, IPR2016-01303, Ex.1019 U.S. Pat. No. 6,501,052 ("Cox"), Jun. 28, 2016.
Nu Mark LLC, IPR2016-01303, Ex.1020 U.S. Pat. No. 6,491,233 ("Nichols"), Jun. 28, 2016.
Nu Mark LLC, Petition for Inter Partes Review of U.S. Pat. No. 9,326,548—IPR2016-01641, Paper 1, Aug. 18, 2016.
Nu Mark LLC, IPR2016-01641, Ex. 1001 U.S. Pat. No. 9,326,548 (the "548 Patent"), Aug. 18, 2016.
Nu Mark LLC, IPR2016-01641, Ex. 1002 File History for U.S. Pat. No. 9,326,548, Aug. 18, 2016.
Nu Mark LLC, IPR2016-01641, Ex. 1003 Declaration of John M. Collins, Ph.D., Aug. 18, 2016.
Nu Mark LLC, IPR2016-01641, Ex. 1004 Curriculum Vitae of Dr. John M. Collins, Aug. 18, 2016.
Nu Mark LLC, IPR2016-01641, Ex. 1005 U.S. Pat. App. Pub. No. 2009/0095311 A1 ("Han 311"), Aug. 18, 2016.
Nu Mark LLC, IPR2016-01641, Ex. 1006 File History for U.S. Appl. No. 13/079,937 (issued as U.S. Pat. No. 8,365,742), Aug. 18, 2016.
Nu Mark LLC, IPR2016-01641, Ex. 1007 Substitute Specification filed in U.S. Appl. No. 13/079,937 (issued as U.S. Pat. No. 8,365,742), Aug. 18, 2016.
Nu Mark LLC, IPR2016-01641, Ex. 1008 U.S. Pat. No. 8,365,742 (the "742 Patent"), Aug. 18, 2016.
Nu Mark LLC, IPR2016-01641, Ex. 1009 U.S. Pat. No. 8,156,944 (the "944 Patent"), Aug. 18, 2016.
Nu Mark LLC, IPR2016-01641, Ex. 1010 File History for U.S. Pat. No. 8,156,944, Aug. 18, 2016.
Nu Mark LLC, IPR2016-01641, Ex. 1011 Institution Decision, *VMR Prods. LLC* v. *Fontem Holdings 1 B.V.*, IPR2015-000859, Paper 9 (P.T.A.B. Sep. 16, 2015), Aug. 18, 2016.
Nu Mark LLC, IPR2016-01641, Ex. 1012 Rulings on Claims Construction, *Fontem Ventures BV et al.* v. *NJOY, Inc. et al.*, No. 2:14-cv-01645, Dkt. 65 (C.D. Cal., Jan. 29, 2015), Aug. 18, 2016.
Nu Mark LLC, Petition for Inter Partes Review of U.S. Pat. No. 9,326,548—IPR2017-00204, Paper 1 Petition, Nov. 4, 2016.
Nu Mark LLC, IPR2017-00204, Ex. 1001 U.S. Pat. No. 9,326,548 (the "548 Patent"), Nov. 4, 2016.
Nu Mark LLC, IPR2017-00204, Ex. 1002 File History for U.S. Pat. No. 9,326,548, Nov. 4, 2016.
Nu Mark LLC, IPR2017-00204, Ex. 1003 Declaration of Dr. John M. Collins ("Collins Decl."), Nov. 4, 2016.
Nu Mark LLC, IPR2017-00204, Ex. 1004 WO 2005/099494 to Hon Lik ("Hon 494") (Int'l App. No. PCT/CN2005/000337, which is the PCT application equivalent of CN2719043Y, "Hon 043"), Nov. 4, 2016.
Nu Mark LLC, IPR2017-00204, Ex. 1005 Certified Translation of WO 2005/099494 ("Hon 494"), Nov. 4, 2016.
Nu Mark LLC, IPR2017-00204, Ex. 1006 U.S. Pat. No. 2,057,353 ("Whittemore"), Nov. 4, 2016.
Nu Mark LLC, IPR2017-00204, Ex. 1007 U.S. Pat. No. 5,894,841 ("Voges"), Nov. 4, 2016.
Nu Mark LLC, IPR2017-00204, Ex. 1008 U.S. Pat. No. 6,155,268 ("Takeuchi"), Nov. 4, 2016.
Nu Mark LLC, IPR2017-00204, Ex. 1009 U.S. Pat. No. 4,947,874 ("Brooks"), Nov. 4, 2016.
Nu Mark LLC, IPR2017-00204, Ex. 1010 IPR2013-00387, Final Written Decision, Paper 43, Nov. 4, 2016.
Nu Mark LLC, IPR2017-00204, Ex. 1011 IPR2015-00859, Institution Decision, Paper 9, Nov. 4, 2016.
Nu Mark LLC, IPR2017-00204, Ex. 1012 *Fontem Ventures, B.V., et al.* v. *NJOY, Inc. et al.*, Case 2:14-cv-01645-GW-MRW, Rulings on Claims Construction (DI-65), Nov. 4, 2016.
Nu Mark LLC, IPR2017-00204, Ex. 1013 Random House Webster's College Dictionary, 1226 (1991), Nov. 4, 2016.
Nu Mark LLC, IPR2017-00204, Ex. 1014 U.S. Pat. No. 2,461,664 ("Smith"), Nov. 4, 2016.
Nu Mark LLC, IPR2017-00204, Ex. 1015 U.S. Pat. No. 3,234,357 ("Seuthe"), Nov. 4, 2016.
Nu Mark LLC, IPR2017-00204, Ex. 1016 U.S. Pat. No. 1,084,304 ("Vaughn"), Nov. 4, 2016.
Nu Mark LLC, IPR2017-00204, Ex. 1017 IPR2016-01297, Patent Owner's Preliminary Response, Paper 8, Nov. 4, 2016.
Nu Mark LLC, IPR2017-00204, Ex. 1018 IPR2016-01288, Ex.2009 to Patent Owner's Preliminary Response, Nov. 4, 2016.
Nu Mark LLC, IPR2017-00204, Ex. 1019 IPR2013-00387, Institution Decision, Paper 7, Nov. 4, 2016.
Nu Mark LLC, IPR2017-00204, Ex. 1020 IPR2016-01268, Patent Owner's Preliminary Response, Paper 8, Nov. 4, 2016.
Nu Mark LLC, IPR2017-00204, Ex. 1021 Certified Translation of CN 201018927Y ("Wang"), Nov. 4, 2016.
Nu Mark LLC, IPR2017-00204, Ex. 1022 WIPO Publication No. WO 2007/078273 ("Liu"), Nov. 4, 2016.
Pan, Fenglin—Request for Invalidation of CN200720148285.9 in Chinese, with English translation of same (citing D1—CN2719043 and D2 CN2084236), Jun. 19, 2013.
Philip Morris Products S.A., Opposition to European Patent No. EP2022349, Apr. 30, 2015.
Philip Morris Products S.A., Observations in EP2022349 Opposition Proceedings, Apr. 15, 2016.
Philip Morris Products S.A., Observations in EP2022349 Opposition Proceedings, Affadavit of Ms. Huixin Guo, Apr. 15, 2016.
Philip Morris Products S.A., Opposition to EP2022349—Additional Observations, Aug. 8, 2016.
Philip Morris Products S.A., Opposition to EP2022349—Additional Observations, Sep. 2, 2016.
Philip Morris Products S.A., Opposition to EP2022349—Additional Observations, Ex. PC.1 to Expert Report (Ping Chai CV), Sep. 2, 2016.

(56) References Cited

OTHER PUBLICATIONS

Philip Morris Products S.A., Opposition to EP2022349—Additional Observations, Ex. PC.2 to Expert Report (excerpts from WO2007131449), Sep. 2, 2016.
Philip Morris Products S.A., Opposition to EP2022349—Additional Observations, Ex. PC.3 to Expert Report (excerpts of report with pub), Sep. 2, 2016.
Philip Morris Products S.A., Opposition to EP2022349—Additional Observations, Expert Report of Ping Chai, Sep. 2, 2016.
Philip Morris Products S.A., Opposition to EP2022349—Additional Observations, High Court decision revoking EP(UK)2022349, Sep. 2, 2016.
Philip Morris Products S.A., Opposition to EP2878215, Jan. 27, 2017.
Philip Morris Products S.A., Opposition to EP2878215, A1—EPO Affidavit-Guo Huixin, Jan. 27, 2017.
Philip Morris Products S.A., Opposition to EP2878215, A2—UK Expert Report of Guo, Jan. 27, 2017.
Philip Morris Products S.A., Opposition to EP2878215, D1—EP2022350A1, Jan. 27, 2017.
Philip Morris Products S.A., Opposition to EP2878215, D2—EP2018886A1, Jan. 27, 2017.
Philip Morris Products S.A., Opposition to EP2878215, D3—U.S. Pat. No. 2,057,353A1, Jan. 27, 2017.
Philip Morris Products S.A., Opposition to EP2878215, D4—EP0893071A1, Jan. 27, 2017.
Philip Morris Products S.A., Opposition to EP2878215, D5—WO2005099494A1, Jan. 27, 2017.
Philip Morris Products S.A., Opposition to EP2878215, D5a—EP1736065A1, Jan. 27, 2017.
Philip Morris Products S.A., Opposition to EP2878215, D6—CN2777995Y, Jan. 27, 2017.
Philip Morris Products S.A., Opposition to EP2878215, D6a—CN2777995Y English Translation, Jan. 27, 2017.
Philip Morris Products S.A., Opposition to EP2878215, D7—U.S. Pat. No. 4,947,874A, Jan. 27, 2017.
Philip Morris Products S.A., Opposition to EP2878215, D8—U.S. Pat. No. 5,894,841A, Jan. 27, 2017.
Philip Morris Products S.A., Opposition to EP2878215, D9—EP0845220A, Jan. 27, 2017.
Philip Morris Products S.A., Opposition to EP2878215, D10—U.S. Pat. No. 3,934,117A, Jan. 27, 2017.
Philip Morris Products S.A., Opposition to EP2878215, D11—U.S. Pat. No. 1,968,509A, Jan. 27, 2017.
Philip Morris Products S.A., Opposition to EP2878215, D12—GB588117A, Jan. 27, 2017.
Philip Morris Products S.A., Opposition to EP2878215, Dec1—Written Decision (EPO), Jan. 27, 2017.
Philip Morris Products S.A., Opposition to EP2878215, Dec2—UK Decision, Jan. 27, 2017.
Philip Morris Products S.A., Opposition to EP2878215, EP1—Opposed Patent EP2878215B1, Jan. 27, 2017.
Philip Morris Products S.A., Opposition to EP2878215, EP2—WO20070131449A1, Jan. 27, 2017.
Philip Morris Products S.A., Opposition to EP2878215, EP2a—EP2022349A1 (Parent application), Jan. 27, 2017.
Philip Morris Products S.A., Opposition to EP2878215, EP2b—WO20070131449A1 English Translation, Jan. 27, 2017.
Philip Morris Products S.A., Opposition to EP2878215, EP2c—EP2878215A1 (published Engl. Language div appl.), Jan. 27, 2017.
Philip Morris Products S.A., Opposition to EP2878215, EP2d—EP2022349B1 (Revoked parent patent), Jan. 27, 2017.
Philip Morris Products S.A., Opposition to EP2878215, EP3—CN2006-20090805Y (CN201067079Y), Jan. 27, 2017.
Philip Morris Products S.A., Opposition to EP2878215, EP3a—CN201067079Y English Translation, Jan. 27, 2017.
Philip Morris Products S.A., Opposition of EP2878215, Additional Observations, Mar. 25, 2019.
Philip Morris Products S.A., Opposition to European Patent No. EP3061359, Jul. 3, 2019.
Philip Morris Products S.A., Opposition to European Patent No. EP2789250, Sep. 26, 2019.
R.J. Reynolds Vapor Company, Answer to Complaint in *Fontem Holdings B.V.* v. *R.J. Reynolds Vapor Company*, 16-CV-2286, Dkt. 027, Jun. 27, 2016.
R.J. Reynolds Vapor Company, Answer to Complaint in *Fontem Holdings B.V.* v. *R.J. Reynolds Vapor Company*, 16-CV-3049, Dkt. 028, Jul. 25, 2016.
R.J. Reynolds Vapor Company, First Amended Answer to Complaint in *Fontem Holdings B.V.* v. *R.J. Reynolds Vapor Company*, 16-CV-2286, Dkt. 033, Jul. 25, 2016.
R.J. Reynolds Vapor Company, Case 16-cv-01255, Preliminary Invalidity Contentions, Mar. 15, 2017.
R.J. Reynolds Vapor Company, Case 16-cv-01255, Preliminary Invalidity Contentions, Exhibit A ('742 patent), Mar. 15, 2017.
R.J. Reynolds Vapor Company, Case 16-cv-01255, Preliminary Invalidity Contentions, Exhibit E ('548 patent), Mar. 15, 2017.
R.J. Reynolds Vapor Company, Case 17-cv-0175, Preliminary Invalidity Contentions, Jul. 31, 2017.
R.J. Reynolds Vapor Company, Case 17-cv-0175, Preliminary Invalidity Contentions, Exhibit H ('632 patent), Jul. 31, 2017.
R.J. Reynolds Vapor Company, *Fontem Holdings B.V.* v. *R.J. Reynolds Vapor Company*, U.S. District Court, Middle District of North Carolina, Case 16-cv-1255 and consolidated cases, Final Invalidity Contentions (relating to U.S. Pat. Nos. 8,365,742, 8,490,628, 8,893,726, 8,899,239, 8,326,548, 8,326,549, and 9,370,205), May 7, 2018.
R.J. Reynolds Vapor Company, *Fontem Holdings B.V.* v. *R.J. Reynolds Vapor Company*, U.S. District Court, Middle District of North Carolina, Case 16-cv-1255 and consolidated cases, Final Invalidity Elections (relating to U.S. Pat. Nos. 8,365,742, 8,490,628, 8,893,726, 8,899,239, 8,326,548, 8,326,549, and 9,370,205), May 7, 2018.
R.J. Reynolds Vapor Company, 16-cv-1255 and consolidated cases, Final Invalidity Contentions, Amended Exhibit A (U.S. Pat. No. 8,365,742), May 7, 2018.
R.J. Reynolds Vapor Company, 16-cv-1255 and consolidated cases, Final Invalidity Contentions, Amended Exhibit E (U.S. Pat. No. 9,326,548), May 7, 2018.
R.J. Reynolds Vapor Company, *Fontem Holdings B.V.* v. *R.J. Reynolds Vapor Company*, U.S. District Court, Middle District of North Carolina, Case 16-cv-1255 and consolidated cases, Final Invalidity Elections (relating to U.S. Pat. Nos. 8,375,957, 8,863,752 9,326,550, 9,326,551, 9,339,062, 8,393,331, 9,364,027, and 9,456,632), May 7, 2018.
R.J. Reynolds Vapor Company, *Fontem Holdings B.V.* v. *R.J. Reynolds Vapor Company*, U.S. District Court, Middle District of North Carolina, Case 16-cv-1255 and consolidated cases, Final Invalidity Contentions (relating to U.S. Pat. Nos. 8,375,957, 8,863,752 9,326,550, 9,326,551, 9,339,062, 8,393,331, 9,364,027, and 9,456,632), May 7, 2018.
R.J. Reynolds Vapor Company, 16-cv-1255 and consolidated cases, Final Invalidity Contentions, Amended Exhibit H (U.S. Pat. No. 9,456,632), May 7, 2018.
R.J. Reynolds Vapor Company, Petition for Inter Partes Review of U.S. Pat. No. 8,365,742—IPR2016-01268, Jul. 2, 2016.
R.J. Reynolds Vapor Company, IPR2016-01268, Ex. 1001 U.S. Pat. No. 8,365,742 to Lik Hon, Jul. 2, 2016.
R.J. Reynolds Vapor Company, IPR2016-01268, Ex. 1002 Chinese Pat. No. 2719043Y to Lik Hon, , Jul. 2, 2016.
R.J. Reynolds Vapor Company, IPR2016-01268, Ex. 1003 Certified English translation of Chinese Pat. No. 2719043Y to Lik Hon, Jul. 2, 2016.
R.J. Reynolds Vapor Company, IPR2016-01268, Ex. 1004 U.S. Pat. No. 2,057,353 to C. L. Whittemore, Jr, Jul. 2, 2016.
R.J. Reynolds Vapor Company, IPR2016-01268, Ex. 1005 Application Data Sheet of Apr. 5, 2011 Filed in U.S. Appl. No. 13/079,937, filed Jul. 2, 2016.
R.J. Reynolds Vapor Company, IPR2016-01268, Ex. 1006 Preliminary Amendment of Apr. 5, 2011 Filed in U.S. Appl. No. 13/079,937, filed Jul. 2, 2016.

(56) References Cited

OTHER PUBLICATIONS

R.J. Reynolds Vapor Company, IPR2016-01268, Ex. 1007 Non-Final Office Action of Jul. 19, 2012 in U.S. Appl. No. 13/079,937, filed Jul. 2, 2016.
R.J. Reynolds Vapor Company, IPR2016-01268, Ex. 1008 Amendment of Aug. 3, 2012 in U.S. Appl. No. 13/079,937, filed Jul. 2, 2016.
R.J. Reynolds Vapor Company, IPR2016-01268, Ex. 1009 PCT Pub. No. WO2007131449, Jul. 2, 2016.
R.J. Reynolds Vapor Company, IPR2016-01268, Ex. 1010 English translation of PCT Pub. No. WO2007131449, Jul. 2, 2016.
R.J. Reynolds Vapor Company, IPR2016-01268, Ex. 1011 Board's Decision Denying Institution in IPR2015-00859, Jul. 2, 2016.
R.J. Reynolds Vapor Company, IPR2016-01268, Ex. 1012 Patent Owner's Preliminary Response to Petition for IPR of U.S. Pat. No. 8,365,742, Jul. 2, 2016.
R.J. Reynolds Vapor Company, IPR2016-01268, Ex. 1013 Petition for IPR of U.S. Pat. No. 8,365,742 in IPR2015-00859, Jul. 2, 2016.
R.J. Reynolds Vapor Company, IPR2016-01268, Ex. 1014 Board's Order Dismissing Petition IPR2015-01587, Jul. 2, 2016.
R.J. Reynolds Vapor Company, IPR2016-01268, Ex. 1015 Declaration of Dr. Robert Sturges, Jul. 2, 2016.
R.J. Reynolds Vapor Company, IPR2016-01268, Ex. 1016 Rohsenow, "Heat, Mass, And Momentum Transfer", Jul. 2, 2016.
R.J. Reynolds Vapor Company, IPR2016-01268, Ex. 1017 WO 2005/099494, which is the PCT application equivalent of Hon (CN 2719043) ("Hon '494"), Jul. 2, 2016.
R.J. Reynolds Vapor Company, IPR2016-01268, Ex. 1018 Certified English translation of WO 2005/099494 pursuant to 37 C.F.R. 42.63(b), Jul. 2, 2016.
R.J. Reynolds Vapor Company, Petition for Inter Partes Review of U.S. Pat. No. 8,365,742—IPR2016-01532, Paper 1, Aug. 5, 2016.
R.J. Reynolds Vapor Company, IPR2016-01532, Ex. 1001 U.S. Pat. No. 8,365,742 to Lik Hon, Aug. 5, 2016.
R.J. Reynolds Vapor Company, IPR2016-01532, Ex. 1002 U.S. Pat. Pub. No. 2009/0095311 to Li Han, Aug. 5, 2016.
R.J. Reynolds Vapor Company, IPR2016-01532, Ex. 1003 Chinese Pat. Appl. No. 200620090805.0, Aug. 5, 2016.
R.J. Reynolds Vapor Company, IPR2016-01532, Ex. 1004 English translation of Chinese Pat. Appl. No. 200620090805.0, Aug. 5, 2016.
R.J. Reynolds Vapor Company, IPR2016-01532, Ex. 1005 PCT publication corresponding to PCT/CN2007/001575, Aug. 5, 2016.
R.J. Reynolds Vapor Company, IPR2016-01532, Ex. 1006 English translation of PCT '575, Aug. 5, 2016.
R.J. Reynolds Vapor Company, IPR2016-01532, Ex. 1007 PCT publication corresponding to PCT/CN2007/001576, Aug. 5, 2016.
R.J. Reynolds Vapor Company, IPR2016-01532, Ex. 1008 English translation of PCT '576, Aug. 5, 2016.
R.J. Reynolds Vapor Company, IPR2016-01532, Ex. 1009 U.S. Appl. No. 12/226,818, filed Oct. 29, 2008, including English translation of the PCT publication (also included as Ex. 1006), Application Data Sheet, and Preliminary Amendment, Aug. 5, 2016.
R.J. Reynolds Vapor Company, IPR2016-01532, Ex. 1010 U.S. Appl. No. 13/079,937 with Preliminary Amendment Filed Apr. 5, 2011, Aug. 5, 2016.
R.J. Reynolds Vapor Company, IPR2016-01532, Ex. 1011 Amendment with Substitute Specification Filed in U.S. Appl. No. 13/079,937 on Aug. 7, 2012, Aug. 5, 2016.
R.J. Reynolds Vapor Company, IPR2016-01532, Ex. 1012 Declaration of Dr. Robert Sturges, Aug. 5, 2016.
R.J. Reynolds Vapor Company, IPR2016-01532, Ex. 1013 Board's Decision Denying Institution in IPR2015-00859, Aug. 5, 2016.
R.J. Reynolds Vapor Company, IPR2016-01532, Ex. 1014 Rulings on Claims Construction, *Fontem Ventures, B.V. et al.* v. *NJOY, Inc. et al.*, No. 2:14-cv-01645 (C.D. Cal., filed Mar. 5, 2014), Aug. 5, 2016.
R.J. Reynolds Vapor Company, IPR2016-01532, Ex. 1015 U.S. Pat. No. 8,156,944, Aug. 5, 2016.

R.J. Reynolds Vapor Company, IPR2016-01532, Ex. 1016 Complaint, *Fontem Ventures B.V. et al.* v. *R.J. Reynolds Vapor Company*, No. 2:16-cv-02286 (C.D. Cal., filed Apr. 4, 2016), Aug. 5, 2016.
R.J. Reynolds Vapor Company, Petition for Inter Partes Review of U.S. Pat. No. 9,326,548—IPR2016-01691, Paper 2, Aug. 30, 2016.
R.J. Reynolds Vapor Company, IPR2016-01691, Ex. 1001 U.S. Pat. No. 9,326,548 to Lik Hon, Aug. 30, 2016.
R.J. Reynolds Vapor Company, IPR2016-01691, Ex. 1002 U.S. Pat. Pub. No. 2009/0095311 to Li Han, Aug. 30, 2016.
R.J. Reynolds Vapor Company, IPR2016-01691, Ex. 1003 Chinese Pat. Appl. No. 200620090805.0, Aug. 30, 2016.
R.J. Reynolds Vapor Company, IPR2016-01691, Ex. 1004 English translation of Chinese Pat. Appl. No. 200620090805, Aug. 30, 2016.
R.J. Reynolds Vapor Company, IPR2016-01691, Ex. 1005 PCT publication corresponding to PCT/CN2007/001575, Aug. 30, 2016.
R.J. Reynolds Vapor Company, IPR2016-01691, Ex. 1006 English translation of PCT '575, Aug. 30, 2016.
R.J. Reynolds Vapor Company, IPR2016-01691, Ex. 1007 PCT publication corresponding to PCT/CN2007/001576, Aug. 30, 2016.
R.J. Reynolds Vapor Company, IPR2016-01691, Ex. 1008 English translation of PCT '576, Aug. 30, 2016.
R.J. Reynolds Vapor Company, IPR2016-01691, Ex. 1009 U.S. Appl. No. 12/226,818, filed Oct. 29, 2008, including English translation of the PCT publication (also included as Ex. 1006), Application Data Sheet, and Preliminary Amendment, Aug. 30, 2016.
R.J. Reynolds Vapor Company, IPR2016-01691, Ex. 1010 U.S. Appl. No. 13/079,937 with Preliminary Amendment Filed Apr. 5, 2011, Aug. 30, 2016.
R.J. Reynolds Vapor Company, IPR2016-01691, Ex. 1011 Amendment with Substitute Specification Filed in U.S. Appl. No. 13/079,937 on Aug. 7, 2012, Aug. 30, 2016.
R.J. Reynolds Vapor Company, IPR2016-01691, Ex. 1012 U.S. Appl. No. 13/740,011, filed Jan. 11, 2013, Aug. 30, 2016.
R.J. Reynolds Vapor Company, IPR2016-01691, Ex. 1013 U.S. Appl. No. 14/244,376 Filed Apr. 3, 2020, Aug. 30, 2016.
R.J. Reynolds Vapor Company, IPR2016-01691, Ex. 1014 Amendment Filed in U.S. Appl. No. 14/244,376 on Nov. 20, 2015, Aug. 30, 2016.
R.J. Reynolds Vapor Company, IPR2016-01691, Ex. 1015 Declaration of Dr. Robert Sturges, Aug. 30, 2016.
R.J. Reynolds Vapor Company, IPR2016-01691, Ex. 1016 Board's Decision Denying Institution in IPR2015-00859, Aug. 30, 2016.
R.J. Reynolds Vapor Company, IPR2016-01691, Ex. 1017 Rulings on Claims Construction, *Fontem Ventures, B.V. et al.* v. *NJOY, Inc. et al.*, No. 2:14-cv-01645 (C.D. Cal., filed Mar. 5, 2014), Aug. 30, 2016.
R.J. Reynolds Vapor Company, IPR2016-01691, Ex. 1018 U.S. Pat. No. 8, 156,944, Aug. 30, 2016.
R.J. Reynolds Vapor Company, IPR2016-01691, Ex. 1019 Complaint, *Fontem Ventures B.V. et al.* v. *R.J. Reynolds Vapor Company*, No. 2:16-cv-03049 (C.D. Cal., filed May 3, 2016), Aug. 30, 2016.
R.J. Reynolds Vapor Company, Petition for Inter Partes Review of U.S. Pat. No. 9,326,548—IPR2016-01692, Paper 2, Aug. 30, 2016.
R.J. Reynolds Vapor Company, IPR2016-01692, Ex. 1001 U.S. Pat. No. 9,326,548 to Lik Hon, Aug. 30, 2016.
R.J. Reynolds Vapor Company, IPR2016-01692, Ex. 1002 Chinese Pat. No. 2719043Y to Lik Hon, Aug. 30, 2016.
R.J. Reynolds Vapor Company, IPR2016-01692, Ex. 1003 Certified English translation of Chinese Pat. No. 2719043Y to Lik Hon, Aug. 30, 2016.
R.J. Reynolds Vapor Company, IPR2016-01692, Ex. 1004 U.S. Pat. No. 2,057,353 to C. L. Whittemore, Jr, Aug. 30, 2016.
R.J. Reynolds Vapor Company, IPR2016-01692, Ex. 1005 WO 2005/099494, which is the PCT application equivalent of Hon (CN 2719043Y) ("Hon '494"), Aug. 30, 2016.
R.J. Reynolds Vapor Company, IPR2016-01692, Ex. 1006 Certified English translation of WO 2005/099494 pursuant to 37 C.F.R. 42.63(b), Aug. 30, 2016.
R.J. Reynolds Vapor Company, IPR2016-01692, Ex. 1007 Application Data Sheet and Specification of U.S. Appl. No. 14/244,376 Filed Apr. 3, 2014, Aug. 30, 2016.

(56) References Cited

OTHER PUBLICATIONS

R.J. Reynolds Vapor Company, IPR2016-01692, Ex. 1008 Non-Final Office Action of Sep. 4, 2014 in U.S. Appl. No. 14/244,376, filed Aug. 30, 2016.
R.J. Reynolds Vapor Company, IPR2016-01692, Ex. 1009 Compilation of prosecution papers filed in U.S. Appl. No. 14/244,376, filed Aug. 30, 2016.
R.J. Reynolds Vapor Company, IPR2016-01692, Ex. 1010 Non-Final Office Action of Aug. 20, 2015 in U.S. Appl. No. 14/244,376, filed Aug. 30, 2016.
R.J. Reynolds Vapor Company, IPR2016-01692, Ex. 1011 Amendment of Nov. 20, 2015 in U.S. Appl. No. 14/244,376, filed Aug. 30, 2016.
R.J. Reynolds Vapor Company, IPR2016-01692, Ex. 1012 Notice of Allowance of Mar. 15, 2016 in U.S. Appl. No. 14/244,376, filed Aug. 30, 2016.
R.J. Reynolds Vapor Company, IPR2016-01692, Ex. 1013 Board's Decision Denying Institution in IPR2015-00859, Aug. 30, 2016.
R.J. Reynolds Vapor Company, IPR2016-01692, Ex. 1014 Board's Order Dismissing Petition IPR2015-01587, Aug. 30, 2016.
R.J. Reynolds Vapor Company, IPR2016-01692, Ex. 1015 Declaration of Dr. Robert Sturges, Aug. 30, 2016.
R.J. Reynolds Vapor Company, IPR2016-01692, Ex. 1016 Rohsenow, "Heat, Mass, and Momentum Transfer", Aug. 30, 2016.
R.J. Reynolds Vapor Company, IPR2016-01692, Ex. 1017 Merriam-Webster Definition of "Set", Aug. 30, 2016.
R.J. Reynolds Vapor Company, IPR2016-01692, Ex. 1018 U.S. Pat. No. 6,155,268 to Takeuchi, Aug. 30, 2016.
R.J. Reynolds Vapor Company, IPR2016-01692, Ex. 1019 U.S. Pat. No. 4,947,874 to Brooks et al., Aug. 30, 2016.
R.J. Reynolds Vapor Company, IPR2016-01692, Ex. 1020 U.S. Pat. No. 4,629,665 to Matsuo, Aug. 30, 2016.
R.J. Reynolds Vapor Company, IPR2016-01692, Ex. 1021 U.S. Pat. No. 5,894,841 to Voges, Aug. 30, 2016.
R.J. Reynolds Vapor Company, IPR2016-01692, Ex. 1022 U.S. Pat. Pub. No. 2005/0016550 to Katase, Aug. 30, 2016.
R.J. Reynolds Vapor Company, IPR2016-01692, Ex. 1023 U.S. Pat. No. 5,703,633 to Gehrer et al., Aug. 30, 2016.
R.J. Reynolds Vapor Company, IPR2016-01692, Ex. 1024 IPR2014-01300, Paper No. 8, Aug. 30, 2016.
R.J. Reynolds Vapor Company, Petition for Inter Partes Review of U.S. Pat. No. 9,456,632—IPR2018-00634, Mar. 1, 2018.
R.J. Reynolds Vapor Company, IPR2018-00634, Ex. 1001: U.S. Pat. No. 9,456,632 ("632 patent"), Mar. 1, 2018.
R.J. Reynolds Vapor Company, IPR2018-00634, Ex. 1002: Expert Declaration of Robert Sturges, Ph.D., Mar. 1, 2018.
R.J. Reynolds Vapor Company, IPR2018-00634, Ex. 1003: U.S. Pat. No. 4,947,874 ("Brooks"), Mar. 1, 2018.
R.J. Reynolds Vapor Company, IPR2018-00634, Ex. 1004: U.S. Pat. No. 2,057,353 ("Whittemore"), Mar. 1, 2018.
R.J. Reynolds Vapor Company, IPR2018-00634, Ex. 1005: U.S. Pat. No. 5,894,841 ("Voges"), Mar. 1, 2018.
R.J. Reynolds Vapor Company, IPR2018-00634, Ex. 1008: U.S. Pat. No. 6,155,268 to Takeuchi, Mar. 1, 2018.
R.J. Reynolds Vapor Company, IPR2018-00634, Ex. 1009: Chinese Pat. No. 2719043Y ("Hon 043") (including certified translation), Mar. 1, 2018.
R.J. Reynolds Vapor Company, IPR2018-00634, Ex. 1010: U.S. Pat. No. 5,743,251 ("Howell"), Mar. 1, 2018.
R.J. Reynolds Vapor Company, IPR2018-00634, Ex. 1011: U.S. Pat. No. 2,461,664 ("Smith"), Mar. 1, 2018.
R.J. Reynolds Vapor Company, IPR2018-00634, Ex. 1012: U.S. Pat. No. 3,234,357 ("Seuthe"), Mar. 1, 2018.
R.J. Reynolds Vapor Company, IPR2018-00634, Ex. 1013: Contact, Merriam-Webster's Collegiate Dictionary, Merriam-Webster, Inc. (11th ed. 2003), Mar. 1, 2018.
R.J. Reynolds Vapor Company, IPR2018-00634, Ex. 1014: U.S. Pat. Pub. No. 2004/0234916 ("Hale"), Mar. 1, 2018.
R.J. Reynolds Vapor Company, IPR2018-00634, Ex. 1015: U.S. Pat. No. 4,922,901 ("Brooks 901"), Mar. 1, 2018.
R.J. Reynolds Vapor Company, IPR2018-00634, Ex. 1016: U.S. Pat. No. 1,084,304 ("Vaughn"), Mar. 1, 2018.
R.J. Reynolds Vapor Company, IPR2018-00634, Ex. 1017: Institution Decision dated Feb. 7, 2017 (Paper 9), *R.J. Reynolds Vapor Co. v. Fontem Holdings 1 B.V.*, IPR2016-01532, (P.T.A.B., petition filed Aug. 5, 2016), Mar. 1, 2018.
R.J. Reynolds Vapor Company, IPR2018-00634, Ex. 1018: Institution Decision dated Mar. 6, 2017 (Paper 9), *R.J. Reynolds Vapor Co. v. Fontem Holdings 1 B.V.*, IPR2016-01691 (P.T.A.B., petition filed Aug. 30, 2016), Mar. 1, 2018.
R.J. Reynolds Vapor Company, IPR2018-00634, Ex. 1019: U.S. Pat. No. 3,292,635 ("Kolodny"), Mar. 1, 2018.
R.J. Reynolds Vapor Company, IPR2018-00634, Ex. 1020: U.S. Pat. No. 3,685,521 ("Dock"), Mar. 1, 2018.
R.J. Reynolds Vapor Company, IPR2018-00634, Ex. 1022: Institution Decision dated Feb. 5, 2018 (Paper 9), *Cascades Canada ULC v. SCA Hygiene Prods AB*, IPR2017-01921 (P.T.A.B., petition filed Aug. 7, 2017), Mar. 1, 2018.
R.J. Reynolds Vapor Company, IPR2018-00634, Ex. 1023: Institution Decision dated Jan. 19, 2018 (Paper 9), *Donghee America, Inc. v. Plastic Omnium Advanced Innovation and Research*, IPR2017-01654 (P.T.A.B., petition filed Jun. 21, 2017), Mar. 1, 2018.
R.J. Reynolds Vapor Company, IPR2018-00634, Ex. 1024: Institution Decision dated May 18, 2017 (Paper 9), *Limelight Networks, Inc. v. Mass. Inst. of Tech.*, IPR2017-00249 (P.T.A.B., petition filed Nov. 11, 2016), Mar. 1, 2018.
R.J. Reynolds Vapor Company, IPR2018-00634, Ex. 1025: Institution Decision dated Jul. 15, 2015 (Paper 10), *Microsoft Corp. v. Parallel Networks Licensing, LLC*, IPR2015-00483 (P.T.A.B., petition filed Dec. 23, 2014), Mar. 1, 2018.
R.J. Reynolds Vapor Company, IPR2018-00634, Ex. 1026: Institution Decision dated Mar. 13, 2013 (Paper 19), *Micron Tech., Inc. v. Bd. of Trs. of the Univ. of Ill.*, IPR2013-00005 (P.T.A.B., petition filed Oct. 2, 2012), Mar. 1, 2018.
R.J. Reynolds Vapor Company, IPR2018-00634, Ex. 1027: Institution Decision dated Jan. 24, 2013 (Paper 18), *Macauto U.S.A. v. BOS GMBH & KG*, IPR2012-00004 (P.T.A.B., petition filed Sep. 16, 2012), Mar. 1, 2018.
R.J. Reynolds Vapor Company, IPR2018-00634, Ex. 1028: Institution Decision dated Feb. 6, 2018 (Paper 8), *Samsung Elecs. Am. v. Uniloc*, IPR2017-01801 (P.T.A.B., petition filed Jul. 20, 2017), Mar. 1, 2018.
R.J. Reynolds Vapor Company, IPR2018-00634, Ex. 1029: Institution Decision dated Jan. 4, 2017 (Paper 11), *R.J. Reynolds Vapor Company v. Fontem Holdings 1 B.V.*, IPR2016-01270 (P.T.A.B., petition filed Jul. 2, 2016), Mar. 1, 2018.
R.J. Reynolds Vapor Company, IPR2018-00634, Ex. 1030: U.S. Pat. Pub. No. 2005/0016550 ("Katase"), Mar. 1, 2018.
R.J. Reynolds Vapor Company, IPR2018-00634, Ex. 1033: U.S. Pat. No. 4,941,486 ("Dube"), Mar. 1, 2018.
R.J. Reynolds Vapor Company, IPR2018-00634, Ex. 1034: U.S. Pat. No. 7,337,782 ("Thompson"), Mar. 1, 2018.
R.J. Reynolds Vapor Company, IPR2018-00634, Ex. 1035: Declaration of Kyle E. Yarberry, Mar. 1, 2018.
R.J. Reynolds Vapor Company, IPR2018-00634, Ex. 1036: WO00/28843 ("Pienemann"), Mar. 1, 2018.
R.J. Reynolds Vapor Company, IPR2018-00634, Ex. 1037: Certified Translation of WO00/28843, Mar. 1, 2018.
Ten Motives Limited, Opposition to European Patent No. EP2022349, Apr. 27, 2015.
VMR Products LLC, Petition for Inter Partes Review of U.S. Pat. No. 8,365,74—IPR2015-00859, Mar. 10, 2015.
VMR Products LLC, IPR2015-00859, Ex. 1001, U.S. Pat. No. 8,265,742, Mar. 10, 2015.
VMR Products LLC, IPR2015-00859, Ex. 1002, Buckner Declaration, Mar. 10, 2015.
VMR Products LLC, IPR2015-00859, Ex. 1003, Buckner CV, Mar. 10, 2015.
VMR Products LLC, IPR2015-00859, Ex. 1004, CN2719043, Mar. 10, 2015.
VMR Products LLC, IPR2015-00859, Ex. 1005, CN2719043—Certified Translation, Mar. 10, 2015.

(56) References Cited

OTHER PUBLICATIONS

VMR Products LLC, IPR2015-00859, Ex. 1006, WO2005099494, Mar. 10, 2015.
VMR Products LLC, IPR2015-00859, Ex. 1007, WO2005099494—Certified Translation, Mar. 10, 2015.
VMR Products LLC, IPR2015-00859, Ex. 1008, CA2562581, Mar. 10, 2015.
VMR Products LLC, IPR2015-00859, Ex. 1009, US20070267031, Mar. 10, 2015.
VMR Products LLC, IPR2015-00859, Ex. 1010, EP0845220, Mar. 10, 2015.
VMR Products LLC, IPR2015-00859, Ex. 1011, U.S. Pat. No. 5,144,962, Mar. 10, 2015.
VMR Products LLC, IPR2015-00859, Ex. 1012, WO2003034847, Mar. 10, 2015.
VMR Products LLC, IPR2015-00859, Ex. 1013, U.S. Pat. No. 2,057,353, Mar. 10, 2015.
VMR Products LLC, IPR2015-00859, Ex. 1014, CV14-1645 Rulings on Claims (litigation proceedings), Mar. 10, 2015.
VMR Products LLC, IPR2015-00859, Ex. 1015, WO2007131449, Mar. 10, 2015.
VMR Products LLC, IPR2015-00859, Ex. 1016, 742 Prosecution History, Preliminary Amendment, Mar. 10, 2015.
VMR Products LLC, IPR2015-00859, Ex. 1017, 742 Prosecution History, Non-final Office Action, Jul. 19, 2012, Mar. 10, 2015.
VMR Products LLC, IPR2015-00859, Ex. 1018, 742 Prosecution History, Amendment, Mar. 10, 2015.
VMR Products LLC, IPR2015-00859, Ex. 1019, 742 Prosecution History, Supplemental Amendment, Mar. 10, 2015.
VMR Products LLC, IPR2015-00859, Ex. 1020, 742 Prosecution History, Examiner Interview Summary, Mar. 10, 2015.
VMR Products LLC, IPR2015-00859, Ex. 1021, 742 Prosecution History, Notice of Allowance, Mar. 10, 2015.
VMR Products LLC, IPR2015-00859, Ex. 1022, 742 Prosecution History, Certificate of Correction, Mar. 10, 2015.
VMR Products LLC, IPR2015-00859, Ex. 1023, Decision—Institution of Inter Partes Review in IPR2013-00387, Paper 7, Mar. 10, 2015.
U.S. District Court, Central District of California, *Fontem Ventures B.V.* v. *NJOY, Inc.*, Case 14-cv-1645-GW-MRW, Dkt. No. 65, Rulings on Claims Construction, Jan. 29, 2015, 28 pgs.
U.S. District Court, Central District of California, *Fontem Ventures B.V.* v. *NJOY, Inc.*, Case 14-cv-1645-GW-MRW, Dkt. 133, Markman Hearing/Claim Construction Final Ruling, May 7, 2015, 16 pgs.
U.S. District Court, Middle District of North Carolina, *Fontem Ventures B.V.* v. *R.J. Reynolds Vapor Company*, Case 16-cv-01255, Dkt. 148, Claim Construction Order, Mar. 12, 2018, 8 pgs.
USPTO PTAB, IPR2013-00387, Paper 7, Decision Instituting Inter Partes Review, Dec. 30, 2013.
USPTO PTAB, IPR2013-00387, Final Written Decision, *CB Distributors, Inc.* and *DR Distributors, LLC* v. *Fontem Holdings 1 B.V.*, U.S. Pat. No. 8,156,944 B2, Dec. 24, 2014.
USPTO PTAB, Inter Partes Review Certificate, IPR2013-00387, Patent No. 8,156,944, Nov. 16, 2018.
USPTO PTAB, IPR2015-00859, Paper 9, Decision Denying Institution, Sep. 16, 2015.
USPTO PTAB, IPR2016-01268, Paper 10, Decision Instituting IPR, Jan. 3, 2017.
USPTO PTAB, IPR2016-01532, Paper 9, Decision Denying IPR, Feb. 7, 2017.
USPTO PTAB, IPR2016-01691, Paper 9, Decision Denying IPR, Mar. 6, 2017.
USPTO PTAB, IPR2016-01692, Paper 8, Decision Instituting IPR, Mar. 7, 2017.
USPTO PTAB, U.S. Appl. No. 12/226,818, Office Action, Apr. 12, 2011, 9 pages.
U.S. Appl. No. 12/226,818, Notice of Allowance, Dec. 6, 2011, 20 pages.
U.S. Appl. No. 13/079,937, Office Action, Jul. 19, 2012.
U.S. Appl. No. 13/079,937, Notice of Allowance, Nov. 14, 2012, 18 pgs.
U.S. Appl. No. 13/740,011, Non-Final Office Action, Jan. 29, 2015.
U.S. Appl. No. 13/740,011, Non-Final Office Action, Jan. 15, 2016.
U.S. Appl. No. 13/740,011, Notice of Allowance, Jun. 21, 2016.
U.S. Appl. No. 13/740,011, Corrected Notice of Allowance, Jun. 29, 2016.
U.S. Appl. No. 14/244,376, Non-Final Office Action, Sep. 4, 2014.
U.S. Appl. No. 14/244,376, Final Office Action, Apr. 29, 2015.
U.S. Appl. No. 14/244,376, Non-Final Office Action, Aug. 20, 2015.
U.S. Appl. No. 14/244,376, Notice of Allowance, Mar. 15, 2016.
U.S. Appl. No. 15/167,659, Non-Final Office Action, Oct. 14, 2016, 9 pgs.
U.S. Appl. No. 15/167,659, Notice of Allowance, Apr. 21, 2017.
U.S. Appl. No. 15/167,659, Corrected Notice of Allowability, Jun. 13, 2017.
U.S. Appl. No. 15/167,659, Corrected Notice of Allowability, Jul. 13, 2017.
U.S. Appl. No. 15/167,659, Corrected Notice of Allowability, Oct. 4, 2017.
U.S. Appl. No. 15/167,690, Non-Final Office Action, Dec. 29, 2016.
U.S. Appl. No. 15/167,690, Non-Final Office Action, Apr. 26, 2017.
U.S. Appl. No. 15/167,690, Non-Final Office Action, Jul. 26, 2018.
U.S. Appl. No. 15/167,690, Non-Final Office Action, Feb. 25, 2019.
U.S. Appl. No. 15/167,690, Non-Final Office Action, Sep. 4, 2019.
U.S. Appl. No. 15/167,690, Final Office Action, Apr. 1, 2020, 29 pages.
U.S. Appl. No. 15/167,690, Advisory Action, Jun. 23, 2020.
U.S. Appl. No. 15/904,217, Non-Final Office Action, Aug. 13, 2018.
U.S. Appl. No. 15/904,217, Non-Final Office Action, Mar. 21, 2019.
U.S. Appl. No. 15/904,217, Notice of Allowance, Aug. 28, 2019.
U.S. Appl. No. 15/904,217, Notice of Allowance, Sep. 2, 2020.
U.S. Appl. No. 15/904,217, Corrected Notice of Allowability, Sep. 30, 2020.
U.S. Appl. No. 15/996,969, Non-Final Office Action, Aug. 15, 2018.
U.S. Appl. No. 15/996,969, Non-Final Office Action, Mar. 7, 2019.
U.S. Appl. No. 15/996,969, Non-Final Office Action, Sep. 13, 2019.
U.S. Appl. No. 15/996,969, Final Office Action, Jan. 10, 2020.
U.S. Appl. No. 15/996,969, Nonfinal Office Action, Dec. 14, 2020.
U.S. Appl. No. 16/846, 189, Nonfinal Office Action, Jul. 22, 2020.
U.S. Appl. No. 16/846, 189, Final Office Action, Oct. 28, 2020.
U.S. Appl. No. 95/002,235, Non-Final Office Action in Inter Partes Reexamination, Nov. 27, 2012.
U.S. Appl. No. 95/002,235, Non-Final Office Action in Inter Partes Reexamination, Cited Ref. 1, CN03111582.9, English Machine Translation corresponding to priority document of Hon '955, Nov. 27, 2012.
U.S. Appl. No. 95/002,235, Non-Final Office Action in Inter Partes Reexamination, Cited Ref. 2, CN200420031182, English Machine Translation corresponding to priority document of Hon '494, Nov. 27, 2012.
U.S. Appl. No. 95/002,235, Non-Final Office Action in Inter Partes Reexamination, Mar. 14, 2018.
U.S. Appl. No. 95/002,235, Right of Appeal Notice in Inter Partes Reexamination, Oct. 16, 2018.
U.S. Appl. No. 95/002,235, U.S. Pat. No. 8,156,944, Inter Partes Reexamination Certificate, Jan. 23, 2019.
EPO, Opposition of EP2022349, Termination of Opposition Proceedings of Patent No. EP2022349 (Application No. 07721148.0) with Revocation of the Patent, Sep. 3, 2021.
EPO, Opposition of EP2789250, Minutes of Oral Proceedings held Apr. 27, 2021, Jun. 23, 2021.
EPO, Opposition of EP2789250, Decision Revoking EP2789250 with Statement of Grounds, Jun. 23, 2021.
EPO, Opposition of EP2789250, Supplemental Documents referred to in Decision Revoking EP2789250 with Statement of Grounds, Jun. 28, 2021.
EPO, Opposition of EP3061359, Decision Revoking EP3061359 with Statement of Grounds and Minutes of Oral Proceedings, Sep. 7, 2021.

(56) References Cited

OTHER PUBLICATIONS

U.S. Appl. No. 16/846,189, Nonfinal Office Action, Sep. 22, 2021.
Philip Morris Products S.A., Opposition of EP2789250, Opposer's Reply to Appeal of Decision Revoking EP2789250, Mar. 4, 2022.
U.S. Appl. No. 16/846,189, Final Office Action, Feb. 2, 2022.

* cited by examiner

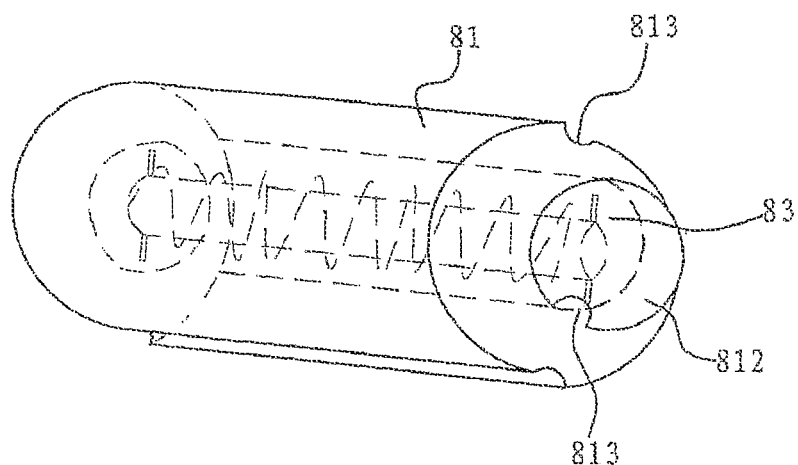
Figure 8
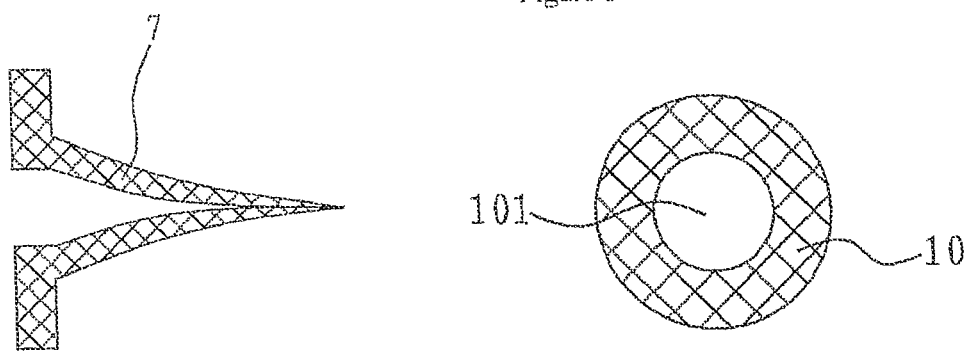
Figure 9
Figure 10
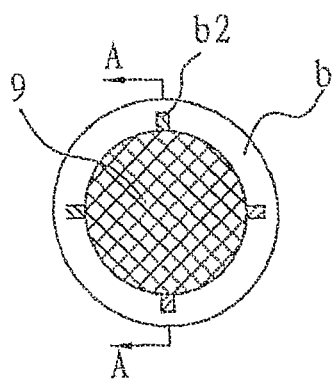
Figure 11
Figure 12

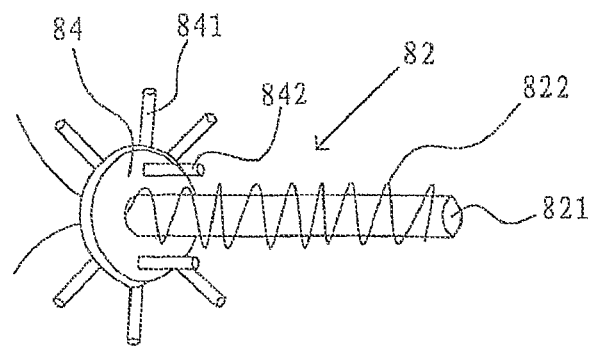
Figure 13
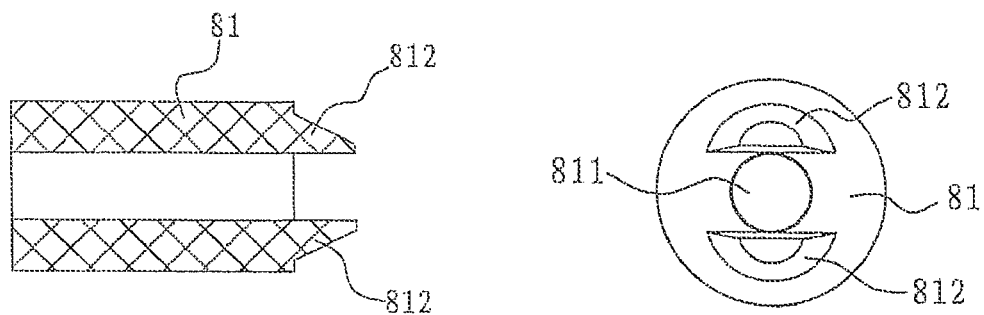
Figure 14
Figure 15
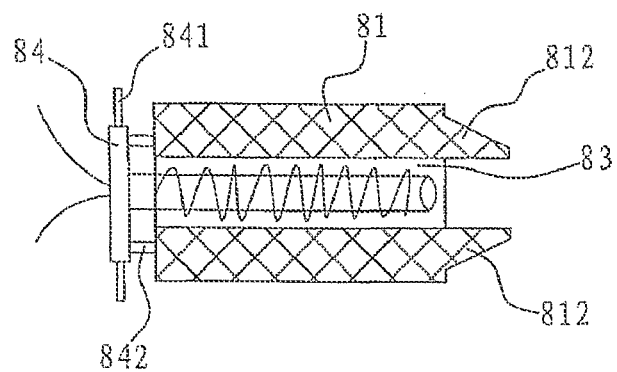
Figure 16

ELECTRONIC CIGARETTE

CROSS-REFERENCE TO RELATED APPLICATIONS

This application is a continuation of U.S. patent application Ser. No. 15/167,690, filed May 27, 2016 and now pending, which is a continuation of U.S. patent application Ser. No. 13/740,011, filed Jan. 11, 2013, now U.S. Pat. No. 9,456,632, which is a continuation of U.S. patent application Ser. No. 13/079,937, filed Apr. 5, 2011, now U.S. Pat. No. 8,365,742, which is a divisional of U.S. patent application Ser. No. 12/226,818, filed Oct. 29, 2008, now U.S. Pat. No. 8,156,944, which is a 371 national filing of International Application No. PCT/CN2007/001575, filed May 15, 2007, which claims priority to Chinese Patent Application No. 200620090805.0, filed May 16, 2006. These applications are incorporated herein by reference.

BACKGROUND ART

Smoking causes serious respiratory system diseases and cancer, though it is hard to persuade the smokers to completely quit smoking.

Nicotine is the effective ingredient in cigarettes. Nicotine acts on the receptor of the central nervous system.

Nicotine is a micromolecular alkaloid, which is basically harmless to human bodies at a small dosage. Plus, its half life period is extremely short in blood. Tar is the major harmful substance in tobacco. Tobacco tar comprises several thousands of ingredients, dozens of which are carcinogenic substances.

To provide cigarette substitutes that contain nicotine but not harmful tar, many products have been used. These products are not as harmful as tar, but are absorbed very slowly. As a result, smokers can't be satisfied in full. In addition, the smokers are deprived of the "smoking" habit.

The electronic cigarettes currently available on the market may resolve the above-mentioned issue, though they are complicated in structure, they don't provide the ideal aerosol effects, and their atomizing efficiency is not high.

SUMMARY OF INVENTION

To overcome the above-mentioned disadvantages, an aerosol electronic cigarette includes a battery assembly, an atomizer assembly and a bottle assembly. The battery assembly connects with the atomizer assembly and both are located in a housing. The bottle assembly is located in one end of the housing and fits with the atomizer assembly.

The battery assembly may include the battery, an operating indicator, electronic circuit board, and airflow sensor, which are connected with the battery, and with the signal output of the airflow sensor connected to the electronic circuit board.

A component for liquid storage of the cigarette bottle assembly stores the nicotine liquid. Smokers can enjoy the feel of smoking, with no fire hazard since there is no need for igniting.

DESCRIPTION OF DRAWINGS

FIG. 8 is the diagram of the atomizer, illustrating the locations of and connection relation between the electric heating rod and porous component.
FIG. 9 is the section view of a check valve.
FIG. 10 is the front section view of a restriction component in a second embodiment.
FIG. 11 is a diagram of the axial structure of the cigarette bottle assembly in another embodiment.
FIG. 12 is a sectional view taken along line A-A of FIG. 11.
FIG. 13 is a diagram of the structure of the electric heating rod of the atomizer in another embodiment.
FIG. 14 is a section view of the porous component of the atomizer in the embodiment shown in FIG. 13.
FIG. 15 is a diagram of the axial structure of FIG. 14.
FIG. 16 is a side section view of the atomizer in the embodiment of FIG. 13, illustrating the locations of and connection relation between the electric heating rod and porous component.

SPECIFIC MODE FOR CARRYING OUT THE INVENTION

Figure 1:
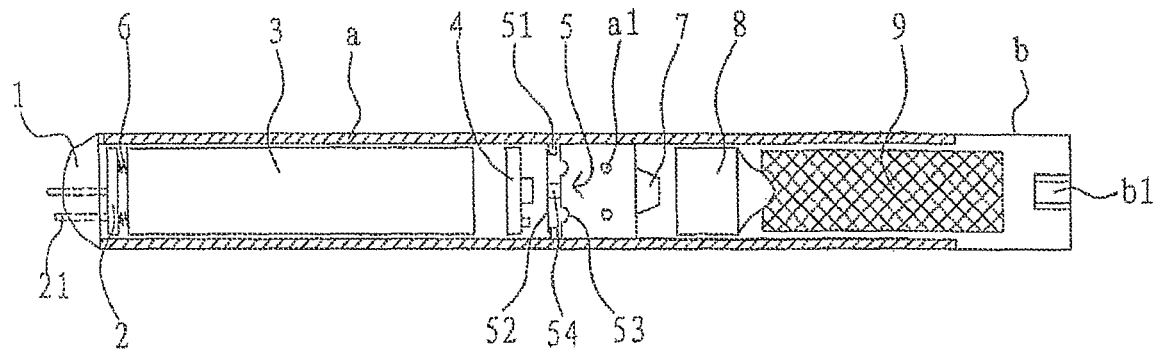
FIG. 1 is the side section view of an electronic cigarette.

As shown in FIGS. 1-10, an aerosol electronic cigarette includes a battery assembly, an atomizer assembly and a cigarette bottle assembly, and also includes a shell or housing (a), which is hollow and integrally formed. The battery assembly connects with the atomizer assembly and both are located in the shell. The cigarette bottle assembly is located in one end of the shell, which is detachable. The cigarette bottle assembly fits with the atomizer assembly. The shell has through-air-inlets (a1).

In this specific embodiment, the battery assembly includes the battery, and the operating indicator (1), electronic circuit board (4), and airflow sensor (5), which are connected with the battery. It also includes a check valve (7). The signal output of the airflow sensor (5) is connected with the said electronic circuit board (4). The battery is a rechargeable battery (3), which may be either a rechargeable polymer lithium ion battery or a rechargeable lithium ion battery. The airflow sensor (5) may be alternatively a semiconductor force-sensitive chip capacitance sensor or an inductance sensor.

The rechargeable battery (3) has a flexibly connected charging plug (2). The blades (21) of the charging plug (2) come out of the other end of the shell (a). Between the charging plug (2) and rechargeable battery (3) is a spring (6), which lies against the body of the rechargeable battery (3) on one end, while its free end lies against the charging plug (2), forming a flexible structure, which buffers the charging plug (2) when plugged for charging, thus protecting the rechargeable battery against any damage. Of course, the rechargeable battery (3) in this embodiment has a charging slot on it, which replaces the structure of charging plug (2) to perform the charging function and protect the rechargeable battery (3) against any damage. The operating indicator (1) is a LED. In this embodiment, there are two LEDs. The electronic circuit board (4) includes an electronic switch circuit, which controls the electric circuit according to the input signals, so that the rechargeable battery (3) electrifies the electric heating rod (82) inside the atomizer (8) and the LEDs as well.

Figure 2:
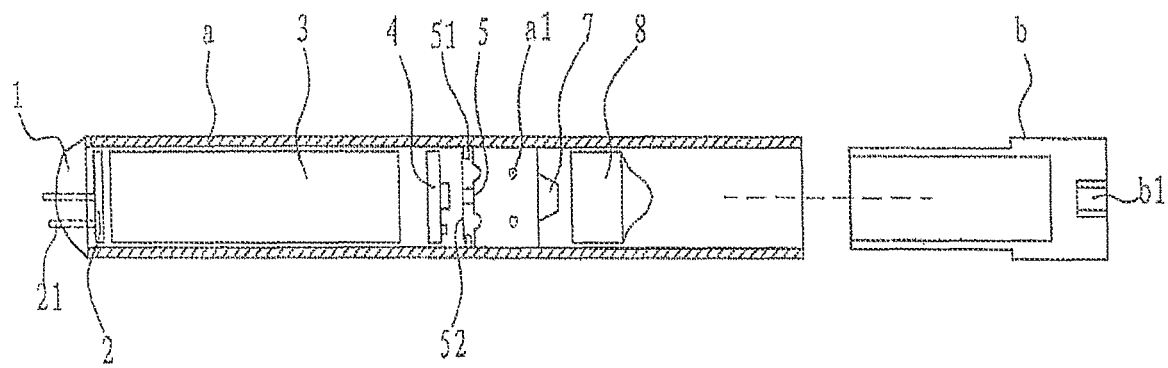
FIG. 2 is the section view of the housing (a) separated from the cigarette bottle assembly.

As shown in FIGS. 1 and 2, the airflow sensor (5) has a silica gel corrugated membrane (53), which connects with magnetic steel (54) with a reed relay (52) on one of its ends. Both ends of the said reed relay (52) correspond to the relay electrodes (51) respectively.

Figure 5:
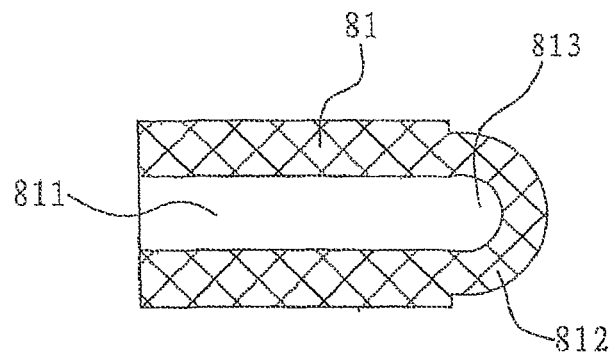
FIG. 5 is the side section view of a porous component of the atomizer.
Figure 6:
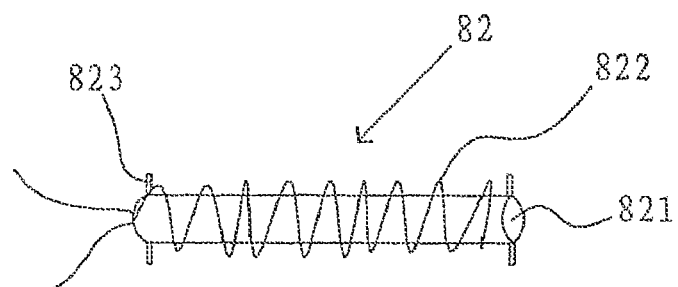
FIG. 6 is the diagram of the structure of an electric heating rod of the atomizer.
Figure 7:
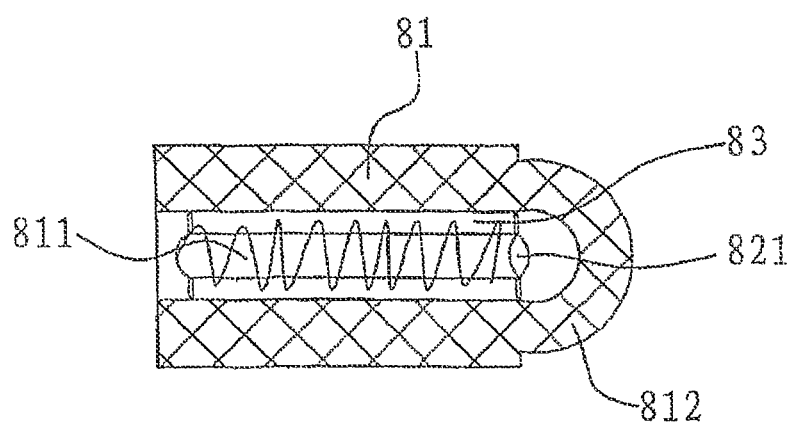
FIG. 7 is the side section of the atomizer, illustrating the locations of and connection relation between the electric heating rod and porous component.

As shown in FIGS. 5-8, the atomizer assembly is an atomizer (8), which includes a porous component (81) and a heating rod (82). The body of the porous component (82) has a run-through atomizing chamber (811). The diameter of the electric heating rod (82) is less than the diameter of the atomizing chamber (811). The electric heating rod (82) enters into the atomizing chamber (811), and there is a clearance between the electric heating rod (82) and interior wall of the atomizing chamber (811), which forms a negative pressure cavity (83). One end of the porous component (81) fits with the cigarette bottle assembly. As FIGS. 5, 7 and 8 show, the porous component (81) has a protuberance (812) on the other end, and the protuberance (812) fits with the cigarette bottle assembly. The protuberance (812) is a protruding half sphere, on the side of which there is a run-through hole (813) connecting to the atomizing chamber (811). Of course, the protuberance (812) may also be a taper, rectangle or any other shape. The porous component (81) is made of foamed nickel, stainless steel fiber felt, macromolecular polymer foam or foamed ceramics, providing the remarkable capabilities in liquid absorption and diffusion, and the ability to absorb the liquid stored in the cigarette bottle assembly.

As shown in FIG. 6, the electric heating rod (82) includes a cylinder (821). The heating wire (822) is wound on the wall of the cylinder (821). On the wall of both ends of the cylinder (821), there are mandrils (823) respectively, which lie against the interior wall of the atomizing chamber (811) of the porous component (81). There is a negative pressure cavity (83) between the electric heating rod and interior wall of the atomizing chamber.

The heating wire is made of platinum wire, nickel-chromium alloy wire or iron-chromium alloy wire containing rare earth, or is flaked. The electric heating rod (82) may alternatively have on its peripheral wall the heating layer made of electrically conductive ceramic PTC material, to replace the heating wire.

In this embodiment, the battery assembly and atomizer assembly are mutually connected and then installed inside the integrally formed shell (a) to form a one-piece part. The rechargeable battery (3) may be charged without frequent change of battery. The user just needs to plug the cigarette bottle assembly into the open end of the shell (a), for easy use and very easy change.

Figure 3:
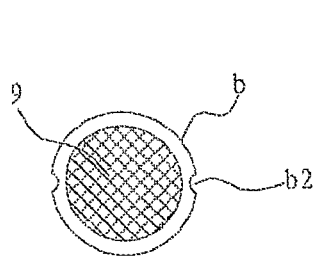
FIG. 3 is the diagram of the axial structure of the cigarette bottle assembly, illustrating the ventilating groove on the peripheral surface of the cigarette holder housing.
Figure 4:
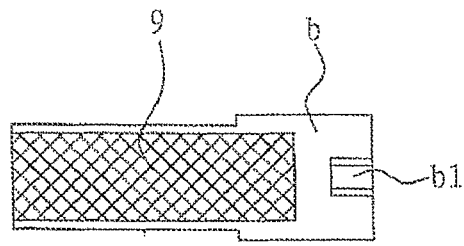
FIG. 4 is the side section view of the cigarette bottle assembly, illustrating the structure of the air channel.

As shown in FIGS. 3 and 4, the cigarette bottle assembly includes a hollow cigarette holder shell (b), and a perforated component for liquid storage (9) inside the shell (b). The perforated component for liquid storage (9) is made of such materials as PLA fiber, terylene fiber or nylon fiber, which are suitable for liquid storage. Alternatively, it may be plastic foam molding or column of multi-layer plates made through plastic injection with polyvinyl chloride, polypropylene and polycarbonate. One end of the cigarette holder shell (b) plugs into the shell (a), and the outer peripheral surface of the cigarette holder shell (b) has an inward ventilating groove (b2). On one end surface of the cigarette holder shell (b), there is an air channel (b1) extending inward. The air channel (b1) is located in the center on the surface of one end of shell (b).

As shown in FIGS. 1-9, one end of the porous component (81) lies against one end surface of the perforated component for liquid storage (9), and contacts the perforated component for liquid storage (9). It absorbs the cigarette liquid from the perforated component for liquid storage (9). When the smoker smokes, the cavity of the cigarette holder shell (b) is in the negative pressure state. In the shell (b), one end of the airflow sensor (5) forms a normal pressure cavity, while the other end forms a negative pressure cavity. The air pressure difference between the normal pressure cavity and negative pressure cavity or the high-speed airflow enables the magnetic steel (54) of the airflow sensor (5) to drive the reed relay (52) to contact the relay electrode (51).

Figure 20:
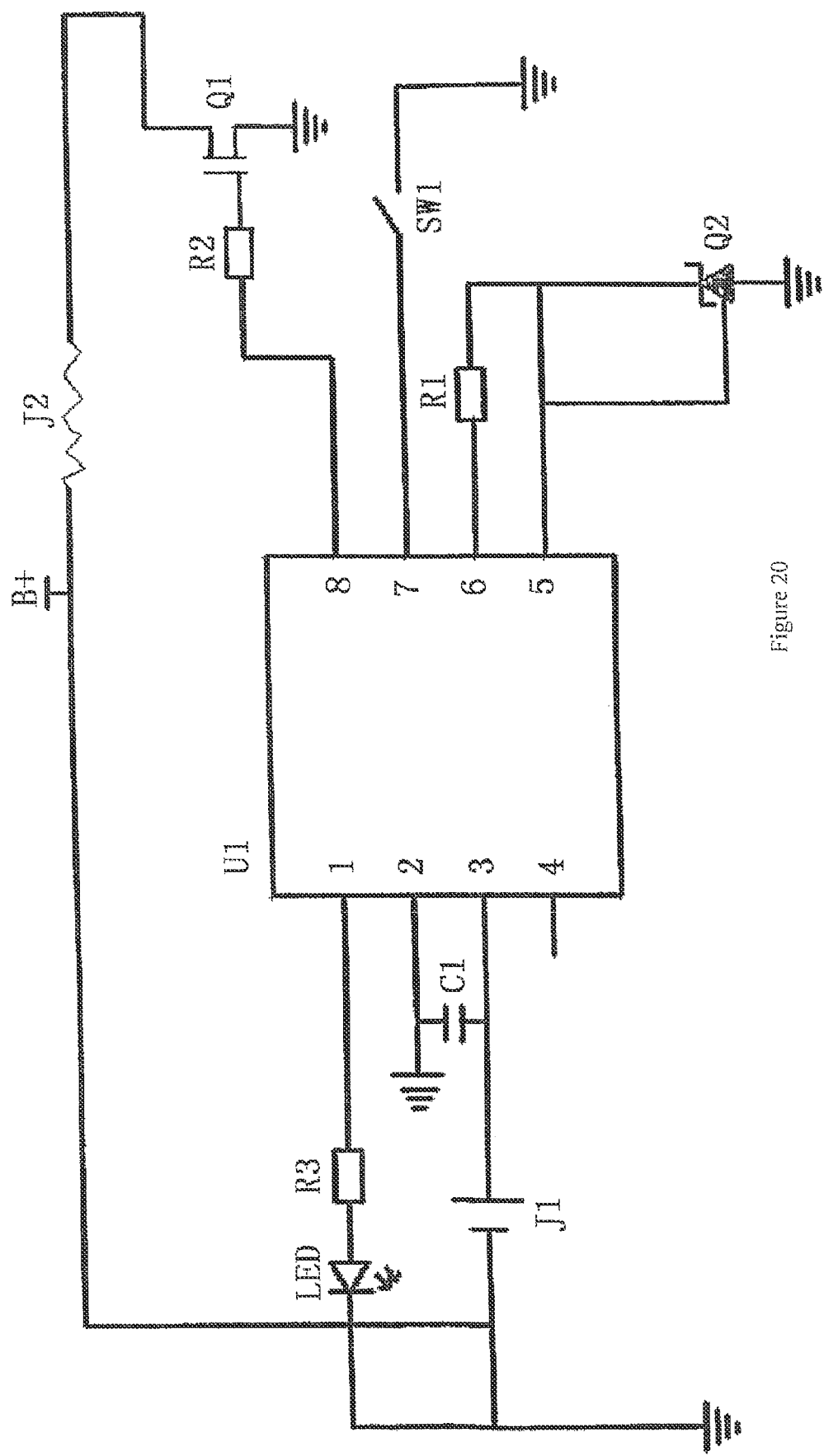
FIG. 20 is the electric circuit diagram of an electronic cigarette.

As shown in FIG. 20, the electric circuit is electrified, and the electronic switch circuit on the electronic circuit board (4) is electrified. Thus, the rechargeable battery (3) starts to electrify the electric heating rod (82) inside the atomizer (8), and at the same time, the LEDs, which are electrified by the rechargeable battery (3), emit light. The air enters the normal pressure cavity through the air inlet (a1), passes the check valve (7) via the airflow passage in the airflow sensor (5), and flows to the negative pressure cavity (83) in the atomizer (8). Since the negative pressure cavity (83) provides the negative pressure compared with the outside, the air flow sprays into it, bringing the cigarette liquid from the porous component (81) to spray into the negative pressure cavity (83) in the form of fine drops.

In the meantime, the electric heating rod (82) is electrified by the rechargeable battery (3) under the control of electronic circuit board (4), to heat the fine drops for atomization. After atomization, the big-diameter fine drops are re-absorbed by the porous component (81) under the action of vortex, while the small-diameter fine drips are suspended in the airflow to form aerosol, which is discharged through the negative pressure cavity (83) and run-through hole (813), flows into the cigarette holder shell (b) of the cigarette bottle assembly, and is absorbed by the air channel (b1). When the aerosol enters the cigarette holder shell (b), multiple small liquid drops are condensed into bigger ones, which fall into the clearance between the cigarette holder shell (b) and air channel (b1) without being absorbed by the air channel (b1). The perforated component for liquid storage (9) of the cigarette bottle assembly and the porous component (81) of the atomizer (8) contact each other to achieve the capillary impregnation for liquid supply.

The unit and its connecting structure of this invention may also be loaded with drugs for delivery to the lung.

Figure 22:
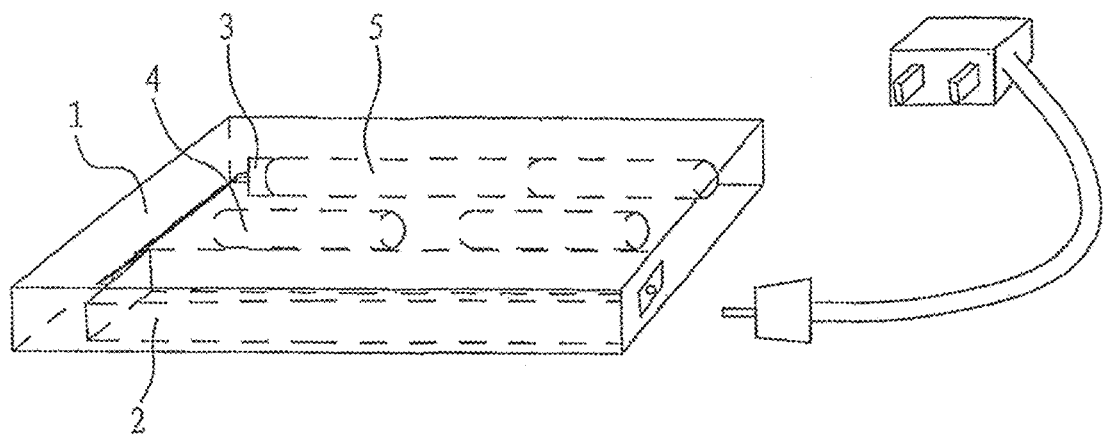
FIG. 22 is a diagram of a charging device, illustrating the locations of and connection relation of various internal parts.
Figure 23:
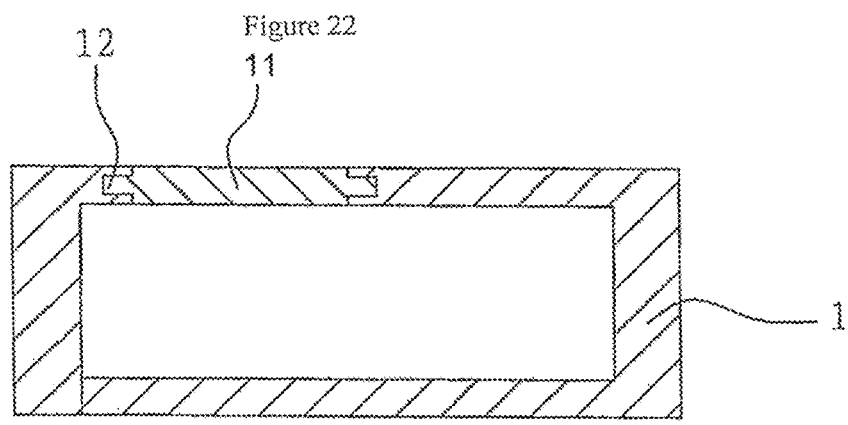
FIG. 23 is the side section view of the charging device.
Figure 24:
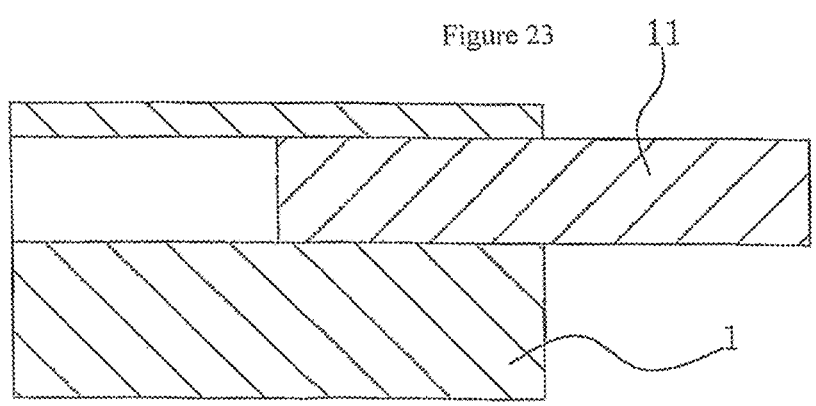
FIG. 24 is the diagram of the front structure of the charging device.

As shown in FIGS. 22, 23 and 24, the electronic cigarette (5) is held in a charging device. The charging device includes a case (1), which contains an auxiliary charging storage battery (2) inside it, and holds the electronic cigarette (5) and the charger (3) for the rechargeable battery embedded in the electronic cigarette (5), as well as the power supply circuit. The power inputs of the auxiliary charging storage battery (2) and charger (3) are connected with the power supply respectively. The charger (3) in this embodiment is a constant voltage & current charger. It may be a GY5210 charger, or any other constant voltage & current charger. The case (1) has a spare liquid supply bottle (4) in it. The power output of the auxiliary charging storage battery (2) is connected with the power input of the charger (3). The power output of the charger (3) is a charging slot (31), which fits with the charging plug of the rechargeable battery inside the electronic cigarette, or a charging plug, which fits with the charging slot of the rechargeable battery.

As shown in FIGS. 23 and 24, on the body of the shell (1), there is a pair of slide ways (12) corresponding to the position of the electronic cigarette, and on the slide ways, there is a slide cover (11).

In the second preferred embodiment, a restriction component (10), which is detachable, is set on one end of the porous component (81). There is a restriction hole (101) on the body of the restriction component (10). The restriction hole (101) corresponds to the atomizing chamber (811). The pore diameter of the restriction hole is less than the inner diameter of the atomizing chamber (811) to the extent that the size of the restriction component (10) installed on the porous component (81) varies, for the purpose of airflow capacity control. On the basis of different applications, the restriction component of different sizes and pore diameters may be used.

In the third preferred embodiment of this utility model, as shown in 11 and 12, on the outer peripheral wall of the cigarette shell (b), there is a protruding rib (b2) that is evenly partitioned. The perforated component for liquid storage (9) enters the cigarette holder shell (b) and lies against the protruding rib (b2). Thus, there appears a clearance between the outer peripheral surface of the perforated component for liquid storage (9) and the interior wall of the shell (b). The clearance is for connection the shell (a) and cigarette holder shell (b). When the user smokes, the air channel (b1) absorbs the air to cause airflow inside the shell (a), thus triggering the airflow sensor (5) and eventually starting the electronic cigarette. Also, the atomizer (8) works to atomize the cigarette liquid and produce gas flow, which enters the cigarette holder shell (b).

In the fourth preferred embodiment, as shown in FIGS. 13, 14, 15 and 16, on one end of the cylinder (821), there is a fixed plate (84), whose outer peripheral wall has partitioned supports (841). The outer ends of the supports (841) lie against the interior wall of the shell (a), thus suspending the cylinder (821), which is connected with the fixed plate (84), in the cavity of the shell (a). On the surface of the fixed plate (84), there is a mandril (842), whose front end lies against one end of the porous component (81), so that the fixed plate (84) is separated from the atomizing chamber (811) of the porous component (81). As a result, the run-through hole on one end of the atomizing chamber (811) won't be blocked, and the mist generated in the atomizing chamber (811) can be dispersed. One end of the porous component (81) has two protuberances (812) at the outlet of the atomizing chamber (811). Between the two protuberances (812) is a clearance. The two protuberances (812) lie against the perforated component for liquid storage (9).

Figure 17:
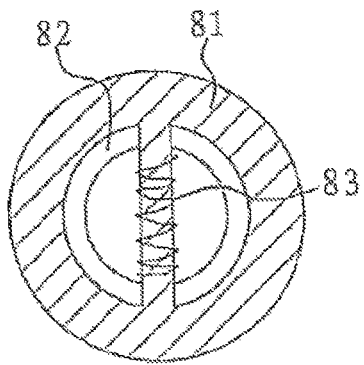
FIG. 17 is a diagram of the axial structure of the atomizer in another embodiment.
Figure 18:
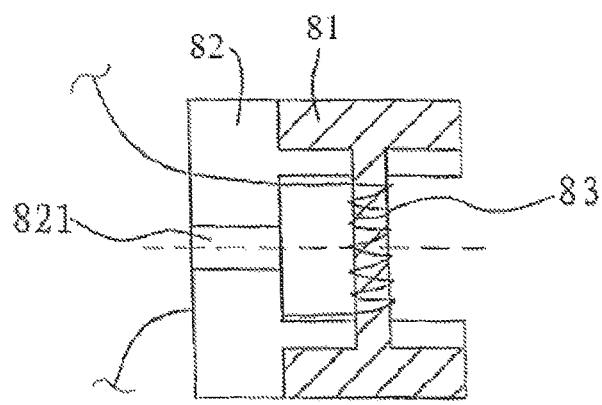
FIG. 18 is the side section view of the atomizer shown in FIG. 17.

In the fifth preferred embodiment, as shown in FIGS. 17 and 18, the atomizer assembly is an atomizer (8), which includes a frame (82), the porous component (81) set on the frame (82), and the heating wire (83) wound on the porous component (81). The frame (82) has a run-through hole (821) on it. The porous component (81) is wound with heating wire (83) in the part that is on the side in the axial direction of the run-through hole (821). One end of the porous component (81) fits with the cigarette bottle assembly. The porous component (81) is made of foamed nickel, stainless steel fiber felt, macromolecular polymer foam or foamed ceramics.

Figure 19:
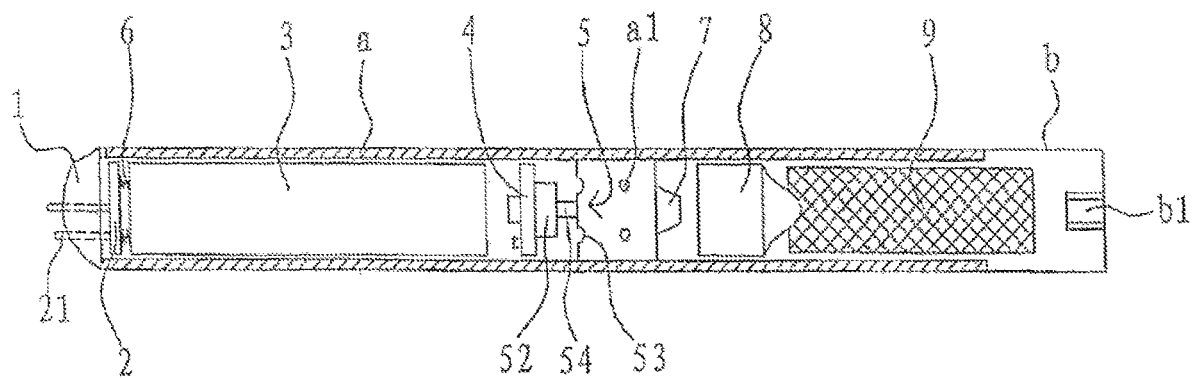
FIG. 19 is the side section view of another electronic cigarette embodiment.
Figure 21:
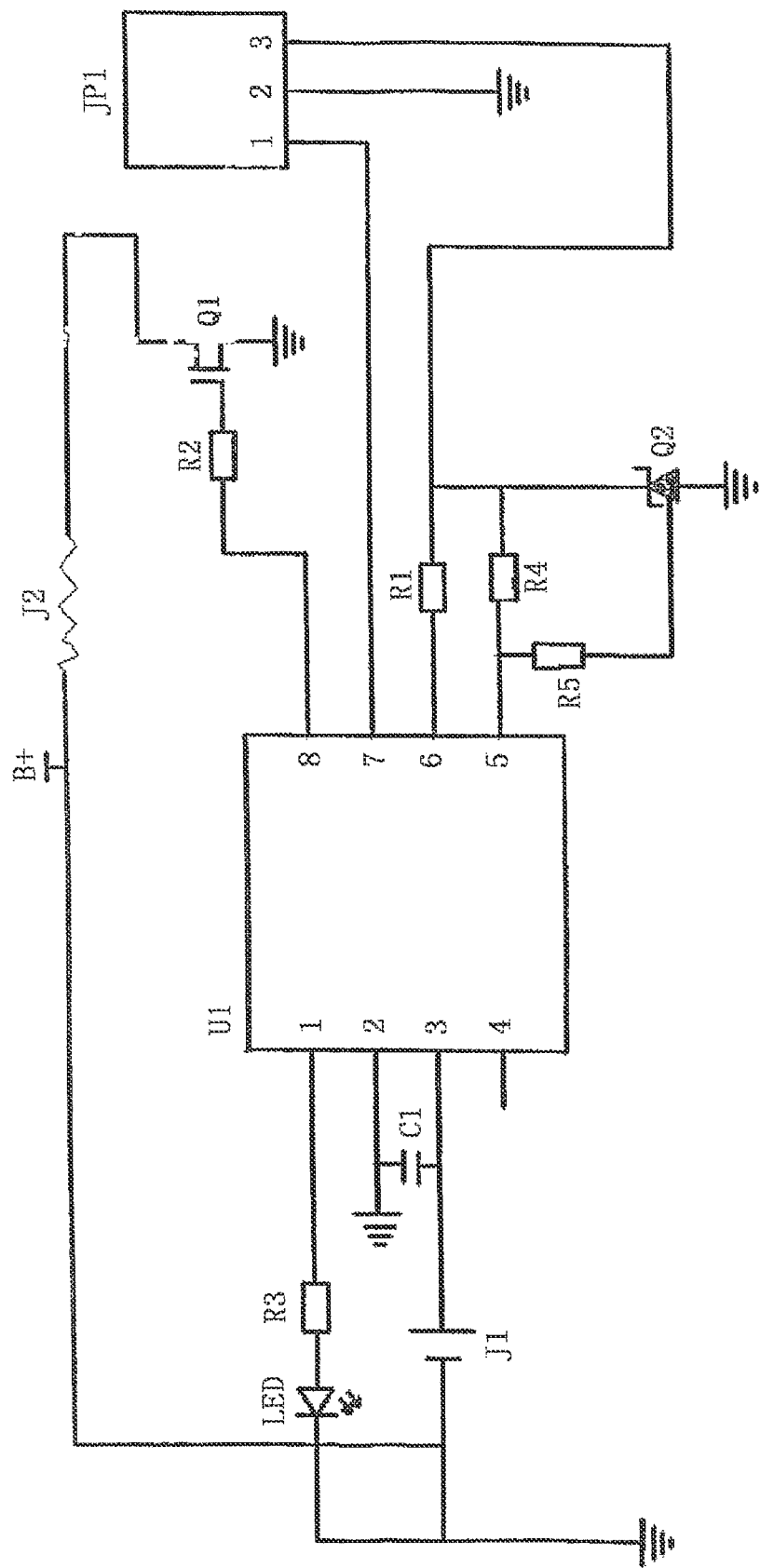
FIG. 21 is another electric circuit diagram of an electronic cigarette.

In the sixth preferred embodiment, as shown in FIG. 19, the airflow sensor (5) has a silica gel corrugated membrane (53), which connects with magnetic steel (54) with a Hall element (52), or a magneto-diode or a magneto-triode on one of its ends. FIG. 21 shows the electric circuit of the electronic cigarette of this solution.

The invention claimed is:
1. An electronic cigarette, comprising:
a battery assembly having a battery and an operating indicator;
an atomizer assembly in a housing;
the atomizer assembly including a ceramic porous component set on a front end of a frame inside of the housing, the ceramic porous component having a cavity, the cavity having an open first end and an obstructed second end;
liquid stored in the housing contacting the ceramic porous component;
the atomizer assembly having a heating element on the ceramic porous component, the heating element electrically connected to the battery assembly, the heating element oriented perpendicular to a longitudinal axis of the housing; and
an air flow path in the atomizer assembly in part parallel to the longitudinal axis of the housing;
wherein the frame has a run-through hole and the air flow path extends through the run-through hole to an outlet.
2. The electronic cigarette of claim 1 wherein the heating element comprises a heating layer made of a conductive material.
3. The electronic cigarette of claim 1 further including an airflow sensor electrically connected to an electronic circuit board in the housing.
4. The electronic cigarette of claim 1 wherein the ceramic porous component is configured to absorb the liquid and to move the liquid towards the heating element via capillary action.
5. The electronic cigarette of claim 1 wherein the frame has a first section having a first diameter, and a second section having a second diameter less than the first diameter, the second section coaxial with the first section, the second section engaging and aligning the ceramic porous component onto the frame.

* * * * *